(12) United States Patent
DiMaio et al.

(10) Patent No.: US 11,076,925 B2
(45) Date of Patent: Aug. 3, 2021

(54) POSITIONING INDICATOR SYSTEM FOR A REMOTELY CONTROLLABLE ARM AND RELATED METHODS

(71) Applicant: Intuitive Surgical Operations, Inc., Sunnyvale, CA (US)

(72) Inventors: Simon Peter DiMaio, San Carlos, CA (US); Nicholas Leo Bernstein, Cary, NC (US); Paul Millman, San Jose, CA (US); Dinesh Rabindran, Sunnyvale, CA (US); Alec Paul Robertson, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 318 days.

(21) Appl. No.: 16/327,986

(22) PCT Filed: Sep. 7, 2017

(86) PCT No.: PCT/US2017/050536
§ 371 (c)(1),
(2) Date: Feb. 25, 2019

(87) PCT Pub. No.: WO2018/052796
PCT Pub. Date: Mar. 22, 2018

(65) Prior Publication Data
US 2019/0231460 A1    Aug. 1, 2019

Related U.S. Application Data

(60) Provisional application No. 62/396,703, filed on Sep. 19, 2016.

(51) Int. Cl.
*A61B 17/34* (2006.01)
*A61B 34/00* (2016.01)
(Continued)

(52) U.S. Cl.
CPC .......... *A61B 34/35* (2016.02); *A61B 17/3423* (2013.01); *A61B 34/30* (2016.02);
(Continued)

(58) Field of Classification Search
CPC ......... A61B 34/35; A61B 34/30; A61B 50/33; A61B 50/15; A61B 46/00; A61B 34/32;
(Continued)

(56) References Cited

U.S. PATENT DOCUMENTS 7,302,288 B1    11/2007  Schellenberg et al.
8,100,133 B2     1/2012  Mintz et al.
(Continued)

FOREIGN PATENT DOCUMENTS

WO    WO-2014151550 A2    9/2014

OTHER PUBLICATIONS

Partial Supplementary European Search Report for Application No. EP17851346.1 dated Apr. 20, 2020, 16 pages.
(Continued)

*Primary Examiner* — Basil T. Jos
(74) *Attorney, Agent, or Firm* — Fish & Richardson P.C.

(57) ABSTRACT

A robotic system includes a base movable relative to a floor surface and a controllable arm extending from the base. The arm is configured to support and move a tool. The arm has a powered joint operable to position and/or orient the tool. The robotic system further includes a positioning indicator. A processor operates the positioning indicator to direct a manual repositioning of the base relative to the floor surface while the processor is operating the powered joint to maintain the position and/or orientation of the tool during the manual repositioning.

30 Claims, 19 Drawing Sheets

(51) Int. Cl.
*A61B 34/20* (2016.01)
*A61B 34/30* (2016.01)
*A61B 34/32* (2016.01)
*A61B 34/35* (2016.01)
*A61B 46/00* (2016.01)
*A61B 46/10* (2016.01)
*A61B 50/13* (2016.01)
*A61B 50/15* (2016.01)
*A61B 50/33* (2016.01)
*A61B 90/00* (2016.01)
*A61B 90/50* (2016.01)
*B25J 9/16* (2006.01)
*A61B 90/57* (2016.01)

(52) U.S. Cl.
CPC .............. *A61B 34/32* (2016.02); *A61B 46/00* (2016.02); *A61B 46/10* (2016.02); *A61B 50/13* (2016.02); *A61B 50/15* (2016.02); *A61B 50/33* (2016.02); *A61B 90/08* (2016.02); *A61B 90/50* (2016.02); *B25J 9/162* (2013.01); *B25J 9/1676* (2013.01); *B25J 9/1684* (2013.01); *A61B 2090/0808* (2016.02); *A61B 2090/0811* (2016.02); *A61B 2090/3945* (2016.02); *A61B 2090/508* (2016.02); *A61B 2090/571* (2016.02)

(58) Field of Classification Search
CPC ..... A61B 46/10; A61B 90/08; A61B 17/3423; A61B 90/50; A61B 50/13; A61B 2090/3945; A61B 2090/0808; A61B 2090/571; A61B 2090/508; A61B 2090/0811; A61B 34/25; A61B 34/20; A61B 34/70; A61B 2090/064; B25J 9/162; B25J 9/1684; B25J 9/1676
See application file for complete search history.

(56) References Cited

U.S. PATENT DOCUMENTS

| | | |
|---|---|---|
| 2001/0013764 A1 | 8/2001 | Blumenkranz et al. |
| 2002/0128552 A1 | 9/2002 | Nowlin et al. |
| 2005/0166413 A1* | 8/2005 | Crampton .............. B25J 13/088 33/503 |
| 2006/0123546 A1* | 6/2006 | Horton ............... A61G 13/0054 5/613 |
| 2008/0218770 A1 | 9/2008 | Moll et al. |
| 2013/0178868 A1 | 7/2013 | Roh |
| 2014/0052153 A1* | 2/2014 | Griffiths ................. A61B 34/30 606/130 |
| 2016/0113728 A1 | 4/2016 | Piron et al. |

OTHER PUBLICATIONS

International Search Report and Written Opinion for Application No. PCT/US2017/050536, dated Jan. 8, 2018, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

POSITIONING INDICATOR SYSTEM FOR A REMOTELY CONTROLLABLE ARM AND RELATED METHODS

CROSS-REFERENCE TO RELATED APPLICATIONS

This application is a U.S. National Stage Application under 35 U.S.C. § 371 and claims the benefit of International Patent Application No. PCT/US2017/050536, filed on Sep. 7, 2017 which claims the benefit of priority to U.S. Provisional Patent Application No. 62/396,703, filed on Sep. 19, 2016, the disclosures of which are incorporated herein by reference in their entirety.

TECHNICAL FIELD

This specification relates to a positioning indicator system for a remotely controllable arm, and more specifically, for a remotely controllable arm of a robotic system.

BACKGROUND

Robotic systems can include robotic arms to manipulate instruments for performing a task at a work site. The robotic arm can include two or more links coupled together by one or more joints. The joints can be active joints that are actively controlled. The joints can also be passive joints that comply with movement of the active joints as the active joints are actively controlled. Such active and passive joints may be revolute or prismatic joints. The configuration of the robotic arm may then be determined by the positions of the joints, the structure of the robotic arm, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon can operate on a patient from a bedside location or a remote location. Telesurgery refers generally to surgery performed using surgical systems where the surgeon uses some form of remote control, e.g., a servomechanism, to manipulate surgical instrument movements rather than directly holding and moving the instruments by hand. A robotic surgical system usable for telesurgery can include a remotely controllable robotic arm. Operators can remotely control motion of the remotely controllable robotic arm. Operators can also manually move pieces of the robotic surgical system into positions within a surgical environment. For example, a surgeon, a surgical assistant, or other operator can push or pull the equipment by hand such that the equipment moves along a floor surface of the surgical environment.

SUMMARY

In one aspect, a surgical system includes a base movable relative to a floor surface and a remotely controllable arm extending from the base. The arm is configured to support a surgical tool. The arm has a powered joint operable to move the surgical tool when the surgical tool is supported by the remotely controllable arm. The surgical system further includes a positioning indicator and a processor. The processor is communicatively coupled to the positioning indicator and the remotely controllable arm. The processor is configured to operate the positioning indicator to direct a manual repositioning of the base relative to the floor surface, and operate the powered joint to maintain a position (and/or orientation) of a distal portion of the remotely controllable arm during the manual repositioning.

In another aspect, a method includes determining an optimality score based on a pose of a remotely controllable arm of a surgical system. The method further includes generating a human-perceptible indication to direct a manual repositioning of a base of the remotely controllable arm such that the optimality score is greater than a threshold score. The method also includes controlling, based on a remote operator input, movement of the remotely controllable arm to perform a surgical operation while the optimality score is greater than the threshold score.

In another aspect, a method of operating a robotic system comprising a robotic arm extending from a base is featured. The method includes: determining, by a processor, a target base pose of a base; operating, by the processor, a positioning indicator to direct a manual repositioning of the base relative to a floor surface; and operating, by the processor, the robotic arm to maintain a position (and/or orientation) of a distal portion of the arm during the manual repositioning of the base.

In yet another aspect, a non-transitory machine-readable medium includes a plurality of machine-readable instructions. These instructions, when executed by one or more processors associated with a robotic system, are adapted to cause the one or more processors to perform a method. The method may be any of the methods disclosed herein.

Certain aspects include one or more implementations described herein and elsewhere, including any appropriate combination of the implementations described below.

In some implementations, the processor is configured to operate the powered joint to maintain the position (and/or orientation) of the distal portion of the remotely controllable arm during the manual repositioning by: (1) operating the powered joint to maintain the position (and/or orientation) of the distal portion relative to a reference, (2) operating the powered joint to maintain a position (and/or orientation) of a cannula held by the distal portion of the arm relative to a reference, (3) operating the powered joint to maintain a position (and/or orientation) of the surgical tool relative to a reference, etc. In some implementations, the reference is a reference point, such as a point corresponding to a location of an access port on a patient through which the surgical tool is inserted, or is to be inserted. In some implementations, the reference includes one or more reference directions but not a reference location; for example, the one or more reference directions may be based on the three-dimensional orientation of the distal portion immediately prior to a beginning of the repositioning process. In some implementations, the reference includes both a reference location and one or more reference directions when position and one or more orientation(s) are maintained. In some implementations, the reference includes a full reference frame sufficient to define location and orientation in three-dimensional space.

In some implementations, the surgical system includes a setup assembly for attaching the base to a table, where the table configured to support a patient above the floor surface. In some implementations, the surgical system includes a cart supported on the floor surface. The cart, for example, supports the base above the floor surface. In some cases, the surgical system further includes a setup assembly connecting the cart to the base, and the setup assembly includes a passive joint. In some implementations, the positioning indicator is, for example, further controlled by the processor to direct the manual repositioning while the cart is movable relative to the floor surface and the base is movable relative to the cart. In some cases, the surgical system further includes a braking mechanism coupled to the cart. The braking mechanism is, for example, controlled by the processor to inhibit movement of the base away from an optimal base location envelope.

In some implementations, the powered joint is a first powered joint. The arm further includes, for example, a second powered joint connected to the first powered joint by a linkage. The first powered joint and the second powered joint are configured, for example, to move the surgical tool, or a cannula, or the distal portion of the arm. The positioning indicator is further controlled by the processor to direct the manual repositioning of the base while the processor is operating the first powered joint and the second powered joint to maintain the position (and/or orientation) of the surgical tool, the cannula, or the distal portion of the arm. The position (and/or orientation) may be maintained relative to any appropriate reference, including as an example relative to a reference point, one or more reference directions, or a reference frame.

In some implementations, the surgical system further includes a selectively releasable passive joint. The passive joint is, for example, connected to the base by a linkage and supports the base above a floor surface. The positioning indicator is further controlled by the processor, for example, to direct the manual repositioning of the base while the processor is operating the powered joint and the selectively releasable passive joint to maintain the position (and/or orientation) of the surgical tool, the cannula, or the distal portion of the arm (such as relative to a reference point, one or more reference directions, or a reference frame.)

In some implementations, the positioning indicator is further controlled by the processor to direct the manual repositioning of the base based on a target range of joint states determined by the processor.

In some implementations, the positioning indicator includes indicator lights selectively activatable by the processor. Each of the indicator lights is, for example, positioned to indicate a corresponding repositioning direction of the manual repositioning of the base.

In some implementations, the positioning indicator is controlled by the processor to direct the manual repositioning by projecting a light toward the floor surface indicative of a repositioning direction of the manual repositioning of the base.

In some implementations, the surgical system further includes sensor to generate a signal indicative of an arm pose of the arm relative to a base pose of the base, wherein the processor is configured to receive the signal to direct the manual repositioning of the base.

In some implementations, the surgical system further includes sensors configured to generate signals indicative of positions of each of the base and the arm. The sensors include, for example, at least one of: a proximity sensor, a proximity sensor, a force sensor, and a pressure sensor.

In some implementations, the surgical system further includes an actuator coupled to the powered joint and controlled by the processor to drive the powered joint. The positioning indicator is controlled by the processor, for example, to direct the manual repositioning of the base while selectively driving the actuator. In some cases, the positioning indicator includes the actuator. The positioning indicator is, for example, controlled by the processor to inhibit movement of the powered joint during the manual repositioning of the base.

In some implementations, the positioning indicator includes a braking mechanism controlled by the processor to provide a tactile indication to direct the manual repositioning of the base. In some cases, the powered joint is movable through a range of joint states. The braking mechanism is, for example, controlled by the processor to direct the manual repositioning of the base by inhibiting movement of the powered joint beyond the range of joint states.

In some implementations, the positioning indicator is further controlled by the processor to direct the manual repositioning of the base based on an optimal base location envelope above the floor surface determined by the processor. In some cases, the positioning indicator is controlled by the processor to alert an operator during the manual repositioning of the base that the base is within the optimal base location envelope. In some cases, the positioning indicator is controlled by the processor to alert an operator during the manual repositioning of the base that the base is outside of the optimal base location envelope. In some cases, the surgical system further includes a sensor positioned on the base and configured to generate a signal indicative of a base pose relative to the optimal base location envelope. The positioning indicator is further controlled by the processor, for example, to direct the manual repositioning of the base based on the signal indicative of the base pose.

In some implementations, the surgical system further includes a sensor to generate a signal indicative of a manual demonstration of a desired range of motion of the arm. The positioning indicator is further controlled by the processor, for example, to direct the manual repositioning of the base based on the signal indicative of the manual demonstration.

In some implementations, the reference point corresponds to a location of an access port on a patient through which the surgical tool is inserted.

In some implementations, the positioning indicator is further controlled by the processor to direct the manual repositioning of the base based on a location of an obstacle on the floor surface relative to the base.

In some implementations, the arm is a first arm. The reference is, for example, a first reference. The surgical system further includes, for example, a second remotely controllable arm configured to support and position (and/or orient) a surgical tool. The second arm has, for example, a powered joint movable to position (and/or orient) the surgical tool of the second arm relative to a second reference. The positioning indicator is further controlled by the processor, for example, to direct the manual repositioning of the base while operating the powered joint of the first arm and the powered joint of the second arm to maintain the position (and/or orientation) of the distal portion of the first arm relative to the first reference and maintain the position (and/or orientation) of the distal portion of the second arm relative to the second reference. In some cases, the positioning indicator is further controlled by the processor to direct the manual repositioning of the base based on a pose of the first arm relative to a pose of the second arm. In some cases, the base is a first base. The surgical system further includes, for example, a second base connected to the second arm. The positioning indicator is further controlled by the processor to, for example, direct a manual repositioning of the first base while operating the powered joint of the first arm to maintain the position (and/or orientation) of the distal portion of the first arm (such as relative to the first reference). The positioning indicator is further controlled by the processor, for example, to direct a manual repositioning of the second base while operating the powered joint of the second arm to maintain the position of distal portion of the second arm (such as relative to the second reference). In some cases, the second arm extends from the base from which the first arm extends.

In some implementations, the positioning indicator is controlled by the processor to direct a first manual repositioning of the base while operating the powered joint to maintain the position (and/or orientation) of the distal portion relative to a first reference before the surgical tool is inserted into an access port of a patient. The positioning indicator is, for example, controlled by the processor to direct a second manual repositioning of the base while operating the powered joint to maintain the position (and/or orientation) of the distal portion relative to a second reference after the surgical tool is inserted into the access port. The second reference can comprise a point corresponding to a position (and/or orientation) of the access port.

In some implementations, the positioning indicator is controlled by the processor to direct the first manual repositioning of the base based on a first optimal base location envelope determined by the processor before the arm is controlled to perform a surgical operation. The positioning indicator is, for example, further controlled by the processor to direct the second manual repositioning of the base based on a second optimal base location envelope determined by the processor after inserting the surgical tool into the access port.

In some implementations, the surgical system further includes a movable table configured to support a patient above the floor surface. The positioning indicator is, for example, controlled by the processor to direct a manual repositioning of the movable table and the manual repositioning of the base while operating the powered joint to maintain the position (and/or orientation) of the distal portion. In some cases, the movable table is connected to the base.

In some implementations, the surgical system further includes a console to receive an operator input and wirelessly transmit a command to the arm to cause movement of the powered joint based on the operator input.

In some implementations, operating the positioning indicator to direct the manual repositioning of the base relative to a floor surface includes: determining an optimality score based on a pose of the robotic arm, operating the positioning indicator to direct the manual repositioning of the base in response to the optimality score not satisfying a optimality criterion, and ceasing operation of the positioning indicator to direct the manual repositioning of the base in response to the optimality score satisfying the optimality criterion.

In some implementations, the processor operates a braking mechanism to inhibit movement of the base away from an optimal base location envelope. In some implementations, operating the robotic arm to maintain the position (and/or orientation) of the distal portion during the manual repositioning of the base includes: operating a powered joint of the robotic arm separately from, or concurrent with, selectively operating a release mechanism of a passive joint of the robotic arm.

In some implementations, operating the positioning indicator to direct a manual repositioning of the base includes any one or more of the following: selectively activating a plurality of indicator lights, projecting a light toward the floor surface indicative of a repositioning direction of the manual repositioning of the base, operating an actuator or a brake to inhibit movement of the robotic arm and provide a tactile indication to direct the manual repositioning of the base, and operating the positioning indicator to indicate that the base is within or outside of an optimal base location envelope.

In some implementations, determining the target base pose of the base includes receiving a signal indicative of a manual demonstration of a desired range of motion of the robotic arm, and using the signal to determine the target base pose. In some implementations, determining the target base pose of the base includes determining the target base pose based on at least one of: a location of an obstacle and a pose of a second robotic arm.

In some implementations, a method of operation further includes: determining, by the processor, a second target base pose of the base, operating the positioning indicator to direct a second manual repositioning of the base relative to the floor surface, and operating the robotic arm to maintain the position (and/or orientation) of the distal portion relative to a second reference during the second manual repositioning of the base relative to the floor surface.

In some implementations, a method of operation further includes: operating the positioning indicator to direct a manual repositioning of a movable table supporting a work piece for robot arm; and operating the robotic arm to maintain a position (and/or orientation) of the distal portion relative to the work piece during the manual repositioning of the movable table.

Advantages of the foregoing may include, but are not limited to, those described below and herein elsewhere. The positioning indicator of the surgical system can aid an operator to manually reposition the base to positions (and/or orientations) that improve performance of the remotely controllable arm during a surgery. The positioning indicator can direct the manual repositioning of the base such that the surgical tool is positioned (and/or oriented) to easily access portions of a workspace about a patient during the surgery. During the manual repositioning, the positioning indicator can direct the operator to move the base toward positions (and/or orientations) that enable joints of the remotely controllable arm to be moved through ranges of motion suitable for the surgery to be performed.

The positioning indicator system can also expedite the manual repositioning process by decreasing an amount of time required to complete the manual repositioning. Without the guidance provided by the positioning indicator system, the operator may reposition the base in directions away from the optimal base location envelope, potentially causing delays due to the sub-optimal positioning (and/or orienting). The positioning indicator system can provide indications that inhibit movement in these directions, thus reducing the amount of time expended to manually reposition the base to preferred positions (and/or orientations).

Because the guidance provided by the positioning indicator system during the manual repositioning occurs while the position (and/or orientation) of the distal portion of the arm is maintained, the steps of repositioning the base can be simplified. For example, the distal portion can be placed such that the surgical tool can be manually positioned or placed into an access port on the patient. The subsequent step of manual repositioning of the base can be decoupled from the step of the placement of the distal portion, as the manual repositioning of the base can occur while the remotely controllable arm is controlled to maintain the position (and/or orientation) of the distal portion. The operator therefore may manually reposition the base without having to manually reposition the distal portion in response to the movement of the base.

Although the specific examples presented in this disclosure often discuss maintaining the position of a distal portion of a controllable arm (or the position of an item supported by the controllable arm, such as a cannula or tool), these techniques are usable to maintain the position and/or orientation of the distal portion of the controllable arm (or an item supported by the controllable arm).

Also, although surgical examples, the techniques disclosed are also applicable to non-surgical use. For example, they may be used with and improve general or industrial robotic operations, such as those use in manipulating work pieces. These techniques may also be used with and improve medical robotic operations for diagnoses and non-surgical treatment.

Further, although the specific examples presented in this disclosure often discuss teleoperational robotic systems and remotely controllable arms, the techniques disclosed are also applicable to robotic systems that are directly and manually moved by operators, in part or in whole. For example, these techniques can be applied to robotic systems designed to help steady a tool held by the robotic arm while the tool is manipulated hand of an operator. As another example, any of the controllable arms discussed herein may be configured to allow direct manipulation, and accept operator instruction through input directly applied to a link or a joint of the manipulator.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
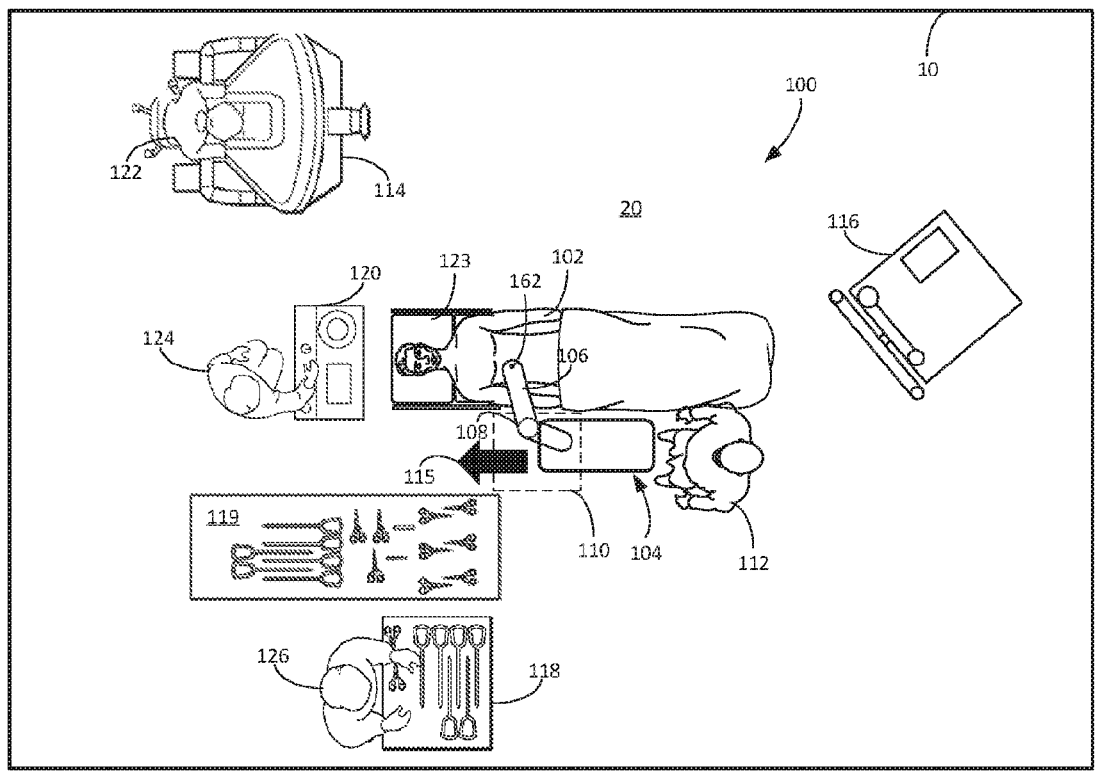
FIG. 1 is a top view of a surgical system in a surgical environment.

Starting with a surgical example, operator or operators (e.g., one or more of surgeons, surgical assistants, nurses, technicians, and other medical practitioners) can operate a surgical system 100, depicted in FIG. 1, to perform a surgery on a patient 102 in a surgical environment 10. The operators can interact with the surgical system 100 to operate a surgical manipulator assembly 104 including a remotely controllable arm 106 to perform the surgery. A surgical tool mounted on the remotely controllable arm 106 can perform the surgery on the patient 102 when the remotely controllable arm 106 is manipulated. The surgical manipulator assembly 104 includes a base 108 supported above a floor surface 20 of the surgical environment 10. The base 108 supports the remotely controllable arm 106 above the floor surface 20 such that, during a surgical operation in which the remotely controllable arm 106 is manipulated to perform the surgery, the remotely controllable arm 106 moves about the surgical environment 10 above the floor surface 20 relative to the base 108. As described in greater detail herein, during various stages of a surgical procedure, the operators may manually reposition the base 108 within the surgical environment 10.

"Reposition" is used with the base herein to indicate changing the position, the orientation, or both the position and orientation of the base.

During the manual repositioning of the base 108 by one or more operators, a distal portion of the remotely controllable arm (or an item supported by the remotely controllable arm, such as a cannula or a surgical tool mounted on the remotely controllable arm 106 and extending distally relative to the remotely controllable arm) can be kept in a desired position and/or orientation within the surgical environment 10. The processor can control the remotely controllable arm 106 to maintain a desired position and/or orientation of the distal portion of the remotely controllable arm (or an item supported by the remotely controllable arm, such as a cannula or a surgical tool). For example, the desired position and/or orientation may be referenced to a frame of reference, and held stationary relative to that frame of reference. Example frames of reference include coordinate frames anchored to specific patient tissue or anatomical feature, to a surface supporting the patient, to the floor surface, to the surgical environment, etc.

"And/or" is used herein to indicate either or both of two stated possibilities. For example, "a position and/or orientation" is used to indicate a position, an orientation, or a combination of both position and orientation parameters.

The position is maintained when the position is kept within an acceptable range of position changes. For example, in some implementations, the acceptable range of position changes is zero, and maintained the position involves keeping the position completely unchanged. In some implementations, the acceptable range of position changes is nonzero, and is based on the limits of the system's design; the position is maintained as close to unchanging as possible given mechanical, electrical, and computational tolerances and errors. In some implementations, the acceptable range of position changes is nonzero, and includes bounds based on operating conditions. For example, in some cases, the acceptable range of position changes is on the order of millimeters or centimeters, and is set to avoid damage to a work piece or human tissue. In some cases, the acceptable range of position changes is larger. In some cases, the acceptable range of position changes differ among different translational degrees of freedom.

Similarly, the orientation is maintained when the orientation is kept within an acceptable range of orientation changes. In various implementations, the acceptable range of orientation changes may be zero, may be a minimal amount limited by system performance, may be less than a degree or multiple degrees or larger, based on performance conditions such as avoiding damage to a work piece or human tissue, and the like. In some cases, the acceptable range of orientation changes differ among different rotational degrees of freedom.

In some implementations, the distal portion of the arm that is maintained in position and/or orientation may include part or all of a distal link of the arm. For example, the distal portion that is maintained may include a distal end of the distal link, may include a portion of the distal link configured to be adjacent an access port during operation, may include a portion of the distal link that couples to a device that mounts to the arm, such as a tool or a cannula, etc.

Similarly, a tool or a cannula that is maintained in position and/or orientation may include part or all of a tool or cannula. For example, a tool or a cannula can be considered to be maintained in position and/or orientation when the position and/or orientation of a particular part of the tool or cannula is maintained. In some cases, a tool or a cannula is maintained in position and/or orientation by maintaining the position and/or orientation of a distal end of the tool or cannula, of a portion of the tool or cannula adjacent to an access port, if a portion of the tool or cannula that coincides with a remote center of rotation of the tool or cannula, etc.

In some implementations, the desired position may be relative to a reference point in the surgical environment 10. For example, the desired position of distal portion of the remotely controllable arm (or an item supported by the remotely controllable arm) can correspond to a pose in which a cannula or a surgical tool or other surgical device would be (or is already) inserted into an access port in the patient 102. An example access port in the patient 102 is a minimally invasive aperture on the patient 102. If the reference point corresponds to the position of the access port on the patient 102, the control of the remotely controllable arm 106 during the manual repositioning enables the remotely controllable arm 106 to remain docked or otherwise proximate to the access port even while the base 108 is being manually repositioned. In some cases, an operator places the remotely controllable arm 106 in a desired position before the manual repositioning of the base 108 occurs. Alternatively, the operator places a device mounted to the remotely controllable arm 106 in a desired position before the manual repositioning of the base 108 occurs. Examples of devices that may be mounted to the remotely controllable arm 106 includes a surgical tool or cannula or other surgical device. During the repositioning of the base 108, the end-effector remains in the desired position with respect to the reference point.

The operators may move the base 108 toward an optimal base location envelope 110 during the manual repositioning. The optimal base location envelope 110, for example, corresponds to a range of three-dimensional positions for the base 108 within the surgical environment 10. When the base 108 is within the optimal base location envelope 110, the remotely controllable arm 106 can be positioned and oriented such that a surgical tool mounted to the remotely controllable arm 106 can easily access areas of the anatomy of the patient 102 relevant to the surgical procedure to be performed or being performed.

To direct the manual repositioning of the base 108 of the remotely controllable arm 106 toward the optimal base location envelope 110, one or more processors of the surgical system 100 can selectively activate a positioning indicator system. The selective activation of the positioning indicator system can indicate to an operator 112 performing the manual repositioning a direction that the base 108 should be moved to reach the optimal base location envelope 110. For example, a visual indication 115 can visually indicate a direction that the operator 112 should move the base 108 of the surgical manipulator assembly 104 such that the base 108 is repositioned toward the optimal base location envelope 110. This technique guides the operator 112 to perform the manual repositioning of the base 108 while the remotely controllable arm 106 is controlled to maintain a pose of the distal portion of the remotely controllable arm 106 (or a pose of an item supported by the remotely controllable arm 106, such as a cannula or a surgical tool).

A pose of the distal portion of a manipulator arm (or of the item held by the manipulator arm) can include a position, an orientation, or any combination of position and orientation parameters, of the distal portion (or of the item). Thus, although the specific examples presented in this disclosure often discuss for simplicity maintaining the position of a distal portion of a controllable arm, the techniques described herein are usable in other respects as well. For example, they may be used to maintain a position, an orientation, or a combination of position and orientation parameters for a distal portion of a controllable arm, or for an item supported by the controllable arm (such as a cannula or tool).

The position and/or orientation may be maintained relative to any appropriate reference. In some implementations, the reference is a reference point, such as a point corresponding to a location of an access port on a patient through which the surgical tool is inserted, or is to be inserted. A single point without orientation information can be sufficient in implementations where only position is maintained. In some implementations, the reference includes one or more reference directions but not a reference location; for example, the one or more reference directions may be based on the three-dimensional orientation of the distal portion immediately prior to a beginning of the repositioning process. A set of direction(s) without a reference location can be sufficient in implementations where only the orientation(s) corresponding to the set of direction(s) are maintained. In some implementations, the reference includes both a reference location and one or more reference directions when position and one or more orientation(s) are maintained. In some implementations, the reference includes a full reference frame sufficient to define location and orientation in three-dimensional space.

Thus, the remotely controllable arm 106 is controlled to maintain one or more position and/or orientation parameters of part or all of the distal portion of the remotely controllable arm 106 (or of an item supported by the remotely controllable arm 106, such as a cannula or tool). For example, in some implementations, the remotely controllable arm 106 is controlled to maintain both the position and orientation of an end effector of the remotely controllable arm 106 or a tool supported by the remotely controllable arm 106. Thus, the positioning indicator system advantageously can enable the remotely controllable arm and associated surgical tools and other instruments or accessories to be optimally positioned and oriented to perform the surgery on the patient 102 when the manual repositioning by the one or more operators is complete.

Example Surgical System

FIG. 1 shows an example of the surgical system 100 including a positioning indicator system to guide the manual repositioning of the base 108 of the surgical manipulator assembly 104. The surgical manipulator assembly 104 includes the remotely controllable arm 106 extending from the base 108. The base 108 is movable relative to the floor surface 20 to enable the operator 112 to perform the manual repositioning. In the example shown in FIG. 1, the operator 112 (e.g., a surgical assistant) guides the base 108 into a position such that the remotely controllable arm 106 of the surgical manipulator assembly 104 can be controlled to perform the surgery.

In some implementations, the surgical system 100 includes one or more of a surgeon's console 114, an electronics cart 116, a tray 118, an accessory table 119 or an anesthesia cart 120. In the example shown in FIG. 1, the patient 102 to be treated is positioned on an operating table 123. A surgeon 122, for example, operates the surgeon's console 114 to control the remotely controllable arm 106 of the surgical manipulator assembly 104 during the surgery. An anesthesiologist or assistant 124 can administer anesthesia from the anesthesia cart 120 to the patient 102 during the surgery, and another assistant 126 can select surgical tools on the tray 118 to be mounted onto the surgical manipulator assembly 104.

To perform the surgery, the surgeon 122 can manipulate the remotely controllable arm 106 of the surgical manipulator assembly 104 by operating the console 114. The console 114 can be positioned within the surgical environment 10 or, in some cases, can be positioned at a remote location outside of the surgical environment 10. The console 114 enables the surgical system 100 to be used for minimally invasive telesurgery. The surgeon 122, for example, operates the surgeon's console 114 to control the remotely controllable arm 106 of the surgical manipulator assembly 104 and manipulate the surgical tool mounted to the remotely controllable arm 106.

In some implementations, the surgeon's console 114 includes a display to enable the surgeon 122 to view a surgical site through images captured by an imaging device. The display is, for example, a stereoscopic display that shows stereoscopic images of the surgical site. While viewing the images of the surgical site, the surgeon 122 can perform the surgical procedures on the patient 102 by manipulating control input devices on the surgeon's console 114, which in turn control motion of the remotely controllable arm 106 of the surgical manipulator assembly 104.

In some implementations, the control input devices of the surgeon's console 114 include manual input devices graspable by hands of the surgeon 122. Manipulation of the manual input devices, for example, causes the surgical manipulator assembly 104 to move the remotely controllable arm 106 on the surgical manipulator assembly 104. Degrees of freedom of the remotely controllable arm 106 are, for example, sufficient to enable the surgeon 122 to manipulate the manual input devices to translate and rotate the remotely controllable arm 106 to perform the surgery. The control input devices, alternatively or additionally, include foot pedals with either or both of toe and heel controls. The surgeon 122 can operate the foot pedals to cause movement or actuation of devices associated with the foot pedals. The surgeon 122 can depress a foot pedal to cause actuation of an end effector. The surgeon's console 114 can include a processor that generates a signal in response to mechanical motion of the control input devices of the surgeon's console 114. The signal in turn can cause corresponding motion of the remotely controllable arm 106 of the surgical manipulator assembly 104.

In some implementations, the electronics cart 116 is connected with the imaging device that generates the images of the surgical site. The surgical manipulator assembly 104, for example, includes the imaging device connected to the electronics cart 116. The imaging device may include illumination equipment (e.g., a Xenon lamp) that provides illumination for imaging the surgical site. The imaging device can capture the images and then transmit the images to the electronics cart 116 for processing. The electronics cart 116 then can transmit the images to the surgeon's console 114 so that the processed images can be presented to the surgeon 122. The electronics cart 116 can include optional auxiliary surgical equipment, such as electrosurgical units, insufflators, suction irrigation instruments, or third-party cautery equipment.

Figure 2A:
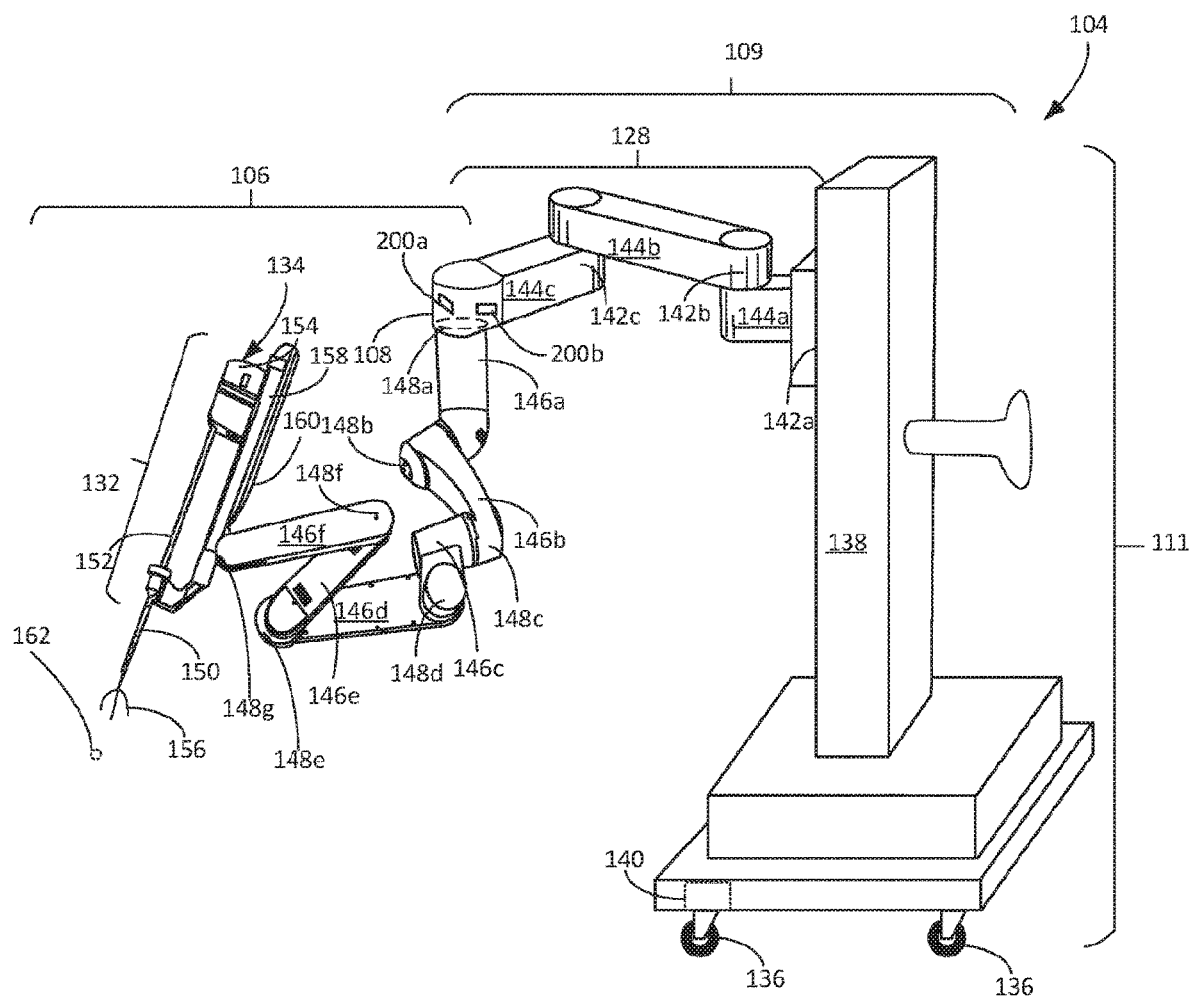
FIG. 2A is a perspective view of a surgical manipulator assembly with indicator lights.

FIG. 2A depicts an example of the surgical manipulator assembly 104. The remotely controllable arm 106 of the surgical manipulator assembly 104 extends from the base 108. The surgical manipulator assembly 104 includes an instrument holder 132 connected to the remotely controllable arm 106 and to which a surgical tool 134 is mounted. The base 108 is movably supported above the floor surface 20 of the surgical environment 10 such that the operator can manually reposition the base 108 above the floor surface 20.

The surgical manipulator assembly 104 includes a setup assembly 109 that supports the base 108 above the floor surface 20. In some implementations, the setup assembly 109 is supported on the floor surface 20 to support the base 108 above the floor surface 20. In some cases, the setup assembly 109 is supported by walls or a ceiling of the surgical environment to support the base 108 of the above the floor surface 20. In some cases, as described herein, the setup assembly 109 is supported by the operating table 123.

As shown in the example of FIG. 2A, the setup assembly 109 is supported on the floor surface. The setup assembly 109 includes a setup arm 128 extending from a cart 111. The cart 111 is, for example, movable omnidirectionally across the floor surface 20. The cart 111 includes, for example, wheels 136 to facilitate a rolling motion of the cart 111 across the floor surface 20. The wheels 136 enable the surgical manipulator assembly 104 to be transported from location to location, such as between operating rooms or within an operating room to position the surgical manipulator assembly 104 near an operating table (e.g., the operating table 123 of FIG. 1). In some implementations, the cart 111 includes a column 138 extending vertically upward when the cart 111 is supported on the floor surface 20. If the cart 111 includes the column 138, the setup arm 128 is connected to the column 138 of the cart 111. In some cases, a braking mechanism 140 is coupled to one or more of the wheels 136. In some cases, the operator manually manipulates the setup assembly 109 and/or the cart 111 to reposition the base 108.

In some examples, the setup arm 128 includes a first setup joint 142a that connects the setup arm 128 to the column 138. The setup arm 128 can include several links connected to one another by joints. In the example depicted in FIG. 2A, the setup arm 128 includes a first setup link 144a, a second setup link 144b, and a third setup link 144c. The setup arm 128 further includes a second setup joint 142b, and a third setup joint 142c. The first joint 142a connects a proximal end of the first setup link 144a to the column 138. The second setup joint 142b connects a distal end of the first setup link 144a to a proximal end of the second setup link 144b. The third setup joint 142c connects a distal end of the second setup link 144b to a proximal end of the third setup link 144c. A distal end of the third setup link 144c is connected to the base 108.

The first joint 142a can be a prismatic joint enabling the setup arm 128, and hence the remotely controllable arm 106, to be translated vertically above the floor surface 20 relative to the cart 111. If the cart 111 includes the column 138, the first joint 142a can connect the setup arm 128 to the column 138 such that the arm 128 can be translated vertically along the column 138. The second and third setup joints 142b-142c can be revolute joints such that any two of the setup links 144a, 144b, 144c connected to one another by one of the joints 142b, 142c can be rotated relative to one another about the connecting joint.

The remotely controllable arm 106 connected to the distal end of the setup arm 128 includes a series of links and joints connected to the instrument holder 132. As depicted in FIG. 2A, the remotely controllable arm 106 includes manipulator links 146a-146f connected to one another in series. A manipulator joint 148a connects the manipulator link 146a to the third setup link 144c. The manipulator joints 148b-148f connect the manipulator links 146a-146f to one another such that the manipulator links 146a-146f can be moved relative to one another. A manipulator joint 146g of the remotely controllable arm 106 movably supports the instrument holder 132.

In the example shown in FIG. 2A, the manipulator joint 148a can also be a revolute joint enabling relative rotation of the remotely controllable arm 106 and the base 108. Each of the manipulator joints 148b-148f can be revolute joints that enable relative rotation between the manipulator links 146a-146f Similarly, the instrument holder 132 can be pivotably coupled to the manipulator link 146f of the remotely controllable arm 106 so that the instrument holder 132 can be rotated relative to the remotely controllable arm 106. The manipulator joint 148g can be a revolute joint that enables the instrument holder 132 to pivot at the manipulator joint 148g and to thereby rotate relative to the remotely controllable arm 106. In some examples, the joint 148g is a wrist joint enabling pivotal motion about two axes.

The instrument holder 132 is configured to hold the surgical tool 134. The instrument holder 132 is also optionally configured to hold a cannula 150, which is a tubular member to be inserted into the access port on the patient 102. The cannula 150 and the surgical tool 134 can each be releasably coupled to the instrument holder 132 so that different types of cannulas and surgical tools can be mounted to the instrument holder 132.

The surgical tool 134 optionally includes a transmission assembly 154 positioned at a proximal end of the elongate shaft 152. The transmission assembly 154 can be actuated to cause motion of an end effector 156 positioned at a distal end of the elongate shaft 152. The end effector 156 of the surgical tool 134 can be controlled in a manner to manipulate tissue of the patient 102, treat tissue, image tissue, or perform other operations during the surgery. The cannula 150 defines a lumen to receive an elongate shaft 152 of the surgical tool 134 such that the elongate shaft 152 can be slidably disposed within the lumen of the cannula 150. The elongate shaft 152 defines a longitudinal axis coincident with a longitudinal axis of the cannula 150. The instrument holder 132 can include an instrument holder carriage 158 translatable along an instrument holder frame 160 such that the elongate shaft 152 of the surgical tool 134 can be translated along its longitudinal axis. The elongate shaft 152 and the end effector 156 can be inserted into and retracted from the lumen of the cannula 150 and the access port on the patient 102 such that the end effector 156 can perform operations during the surgery.

The term "tool" encompasses both general or industrial robotic tools and specialized robotic medical instruments (including robotic surgical instruments and robotic medical instruments for diagnoses and non-surgical treatment). The tool/manipulator interface, e.g., the instrument holder 132, can be a quick disconnect tool holder or coupling, allowing rapid removal and replacement of the tool with an alternate tool. Although the specific examples presented in this disclosure are often surgical examples, the techniques disclosed are also applicable to non-surgical use. For example, they may be used with and improve general or industrial robotic operations, such as those use in manipulating work pieces. These techniques may also be used with and improve medical robotic operations for diagnoses and non-surgical treatment.

Further, although the specific examples presented in this disclosure often discuss teleoperational robotic systems, the techniques disclosed are also applicable to robotic systems that are directly and manually moved by operators, in part or in whole. For example, these techniques can be applied to robotic systems designed to help steady a tool held by the robotic arm while the tool is manually manipulated by an operator. As another example, any of the controllable arms discussed herein, including arms 106, 804A, 804B, 804C, 904, 1000 may be configured to allow direct manipulation, and accept operator instruction through input directly applied to a link or a joint of the controllable arm.

The setup assembly 109, the base 108, and the remotely controllable arm 106 form a kinematic chain to control a surgical tool 134 supported by the remotely controllable arm 106, e.g., supported by the instrument holder 132 of the remotely controllable arm 106. For example, a proximal end of the setup assembly 109 is supported on the floor surface 20, a distal end of the setup assembly 109 is connected to the base 108, the base 108 is connected to a proximal end of the remotely controllable arm 106, and a distal portion 159 of the remotely controllable arm 106 is configured to hold a cannula 150. The setup assembly 109, the base 108, the remotely controllable arm 106 are kinematically connected in series. As a result, movement of one or more joints of the surgical manipulator assembly 104, movement of the cart 111, or movement of both the surgical manipulator assembly 104 and the cart 111 can cause motion of the distal portion 159 (or the cannula 150 or the tool 134 if present and held by the instrument holder 132) relative to the floor surface 20. A portion of the surgical tool 134 extends through cannula 150 when the surgical tool 134 is mounted to the remotely controllable arm 106. Thus, when the surgical tool 134 is mounted to the remotely controllable arm 106, the setup assembly 109, the base 108, the remotely controllable arm 106, and the surgical tool 134 are kinematically connected in series. As a result, movement of a joint of the surgical manipulator assembly 104 or the cart 111 can cause motion of the surgical tool 134 relative to the floor surface 20.

During the surgical operation, the setup assembly 109 can be fixed above the floor surface 20, thereby causing the base 108 to be stationary within the surgical environment 10 above the floor surface 20. Joints of the remotely controllable arm 106 can be manipulated while the setup assembly 109 is fixed to cause motion of the surgical tool 134 to perform the surgery. The surgical manipulator assembly 104 can include a number of degrees of freedom between the setup assembly 109 and the surgical tool 134 such that surgical tool 134 can be placed in a range of possible positions during the surgical operation. Actuation of the end effector 156 (such as opening or closing of the jaws of a gripping device, energizing an electrosurgical paddle, or the like) can be separate from, and in addition to, the degrees of freedom of the remotely controllable arm 106.

The joints of the remotely controllable arm 106 can have sufficient degrees of freedom to move the distal portion 159 close to the access port of the patient 102 such that the cannula 150 and the surgical tool 134 can be inserted through the access port of the patient 102 to perform the surgery. The specific combination of joints described with respect to FIG. 2A is one example of the possible joint and link combinations and the degrees of freedom possible for the remotely controllable arm 106. The revolute joints, which include the joints 142b-142c, 148a-148g, each connect two links to enable the links to rotate relative to one another about a joint axis defined by the revolute joint. The prismatic joints, which include the joint 142a as well as the joint between the instrument holder frame 160 and the instrument holder carriage 158, allow for translation along a joint axis defined by the prismatic joint.

In some implementations, some of the joints 142a-142c, 148a-148g of surgical manipulator assembly 104 are powered joints that can be controlled and actuated to cause relative motion of connecting links. The joints 142a-142c, 148a-148g can be controlled by the surgeon 122 using control inputs on the surgeon's console 114. The surgeon 122, upon manipulating the control inputs on the surgeon's console 114, can cause one or more actuators associated with the joints 142a-142c, 148a-148g to activate, in turn causing two or more links connected by the joints to move relative to one another. For example, the joint 148g movably supporting the instrument holder 132 can be a powered joint that enables the surgeon 122 to cause the end effector 156 to move when the powered joint is actuated. In some implementations, the surgeon 122 or other operator manually interacts with the joints of the surgical manipulator assembly 104 to cause movement of the joints.

In some implementations, some of the joints 142a-142c, 148a-148g are passive joints that are not actively controlled by a processor or processors of the surgical system 100 in response to operator input. The joints 142a-142c, 148a-148g, instead of being actively controlled, can move in response to movement of actively controlled joints. In some examples, the passive joints of the surgical manipulator assembly 104 can be selectively releasable. A passive joint can include a release mechanism that enables motion of the passive joint when activated. For example, the release mechanism can include a releasable clamp that, when operated, causes the passive joint to be released and to be movable. A passive joint can include a braking mechanism that, upon release, allows motion of the joint or, upon actuation, inhibits motion of the joint. In some implementations, the surgeon 136 or other operator manually interacts with the joints of the surgical manipulator assembly 104 to cause movement of the joints.

The remotely controllable arm 106 can have more degrees of freedom than necessary to place the distal portion 159, the cannula 150, or surgical tool 134 in a given position, e.g., can have redundant degrees of freedom. The manipulator linkages can have sufficient degrees of freedom so as to occupy a range of joint states for a given end effector state. Such structures may include linkages having redundant degrees of freedom. For example, in some implementations, the remotely controllable arm 106, the setup arm 128, or the remotely controllable arm 106 and the setup arm 128 together include a plurality of joints that provide sufficient degrees of freedom to allow a range of joint states for (1) a pose of the base 108 and (2) a state of a distal portion of the remotely controllable arm 106 or of an end effector of the surgical tool 134.

"Linkage" is used in this application to indicate a structure including a single link, at least one link, or multiple links as applicable given the context. In these structures, in some implementations, actuation of one joint may be directly replaced by a similar actuation of a different joint along the kinematic chain. These structures are, in some cases, referred to as having excess, extra, or redundant degrees of freedom. These terms can encompass kinematic chains in which, for example, intermediate links can move without changing the pose of an end effector.

In this regard, in this position of the distal portion 159 (or surgical tool 134 if present), each joint of the remotely controllable arm 106 can occupy or be driven between a range of joint states, and each link of the remotely controllable arm 106 can occupy or be driven within a range of alternative linkage positions. In this position of the distal portion 159 (or surgical tool 134 if present), each joint of the remotely controllable arm 106 can have a range of joint velocity vectors or speeds. The ranges of available joint states, the ranges of alternative linkage positions, and the ranges joint velocity vectors or speeds can be defined by the number and types of degrees of freedoms.

The term "state" of a joint can refer to control variables associated with the joint. For example, the state of a revolute joint that enables relative rotation between links can include an angle defined by the joint within a range of motion and/or an angular velocity of the joint. The state of a prismatic joint may refer to an axial position and/or an axial velocity of the joint.

Movement of the remotely controllable arm 106 may be controlled so that the distal portion 159 is constrained relative to the access port (or the surgical tool 134 if present is constrained to a desired motion through the access port). Such motion can include, for example, axial insertion of the elongate shaft 152 through the access port, rotation of the elongate shaft 152 about its longitudinal axis, and pivotal motion of the elongate shaft about a pivot point adjacent the access port.

In some examples, these motions may be inhibited through use of robotic data processing and control techniques of the joints of the remotely controllable arm 106. The joints 148a-148g of the remotely controllable arm 106 can be controlled to maintain a position and/or orientation of the distal portion 159 (or cannula 150 or surgical tool 134 if present). The position and/or orientation may be maintained relative to any appropriate reference; example references include a reference frame anchored to the surgical environment, the floor surface, an anatomical feature of the patient 102, etc. The reference may be defined as such as a reference point 162 in the surgical environment 10. In some examples, only one of the joints of the remotely controllable arm 106 is controlled to maintain a position and/or orientation of the distal portion 159 (or cannula 150 or surgical tool 134 if present) relative to a reference. In some examples, multiple joints of the remotely controllable arm 106 are controlled to maintain the position and/or orientation. The reference may be a reference point 162 in the surgical environment 10. Where the orientation of the distal portion 159 (or cannula 150 or surgical tool 134 if present) is maintained as well, the reference may include a reference frame with an origin at reference point 162.

The reference point 162 can correspond to a remote center of motion constraining motion of the remotely controllable arm 106 (and thus the distal portion 159 or any items supported by the remotely controllable arm 106, such as the surgical tool 134). In particular, the reference point 162 may be a pivot point about which a portion of the remotely controllable arm 106 rotates. In some cases, the reference point 162 may coincide with the access port on the patient 102 such that, as the remotely controllable arm 106 or the surgical tool 134 is moved, the region within which the surgical tool 134 enters into the anatomy of the patient 102 through the access port undergoes little or no motion relative to the reference point 162, thereby reducing stresses on the anatomy of the patient 102 at the reference point 162. The joints 148a-148g can be controlled such that any point along the surgical tool 134 or an associated cannula 150 is rotated about the reference point 162 when the joints 148a-148g are moved. The joints 148a-148g can have sufficient available degrees of freedom such that, when a first set of joints is moved, in response, a second set of joints can be moved to maintain the position and/or orientation of the distal portion 159 (or an item supported by the remotely controllable arm such as a cannula 150 or a surgical tool 134). In some implementations, the joints 148a-148g, or a subset of the joints 148a-148g, have multiple configurations that maintain a particular position and/or orientation of the distal portion 159 (or an item supported by the remotely controllable arm such as a cannula 150 or a surgical tool 134).

In this regard, joints 148a-148g can be moved toward optimum poses within the surgical environment 10 without causing movement of the distal portion 159 (or an item supported by the remotely controllable arm such as a cannula 150 or a surgical tool 134). Other examples of software-constrained remote centers of motion of robotic arms and manipulators are described in U.S. Pat. No. 8,004,229 (herein referred to as "the '229 patent") published on Aug. 23, 2011, the entirety of which is hereby incorporated by reference in its entirety.

Figure 3:
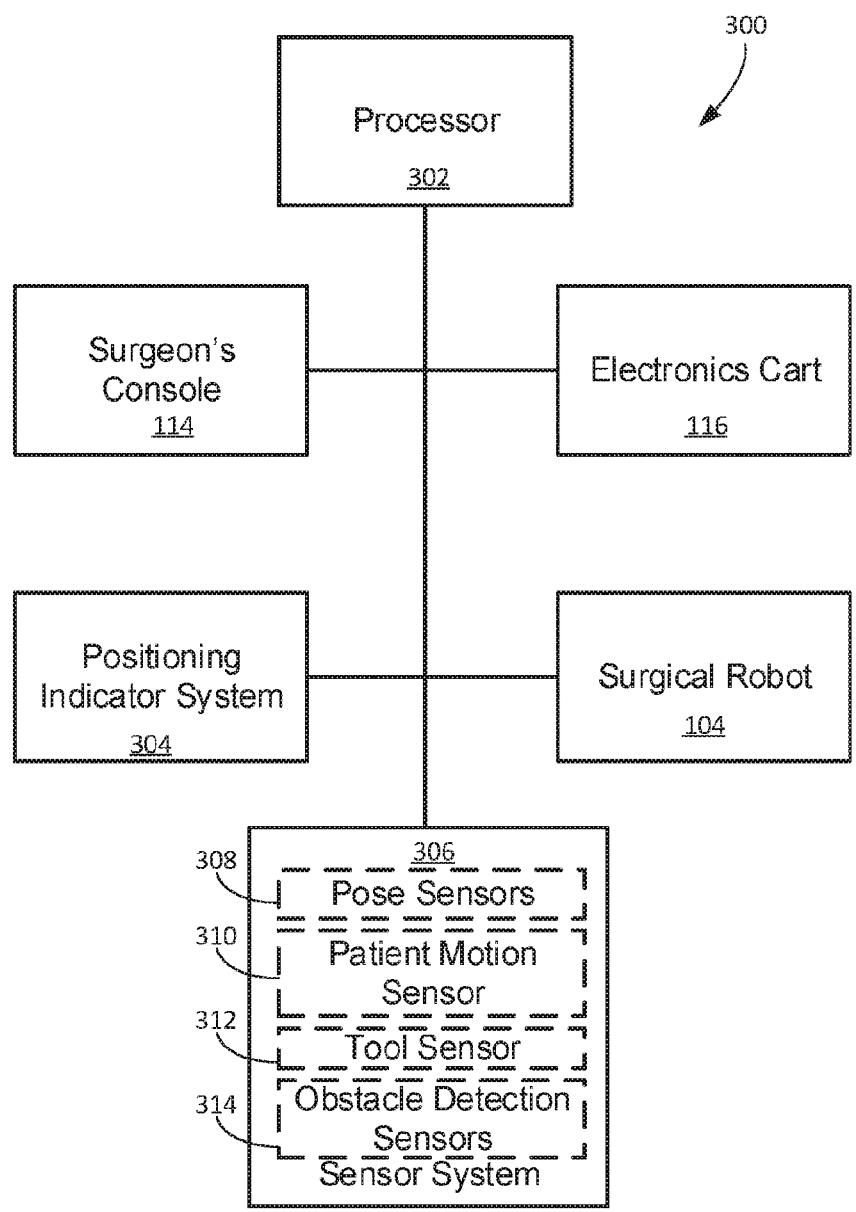
FIG. 3 is a block diagram of a control system for a robotic system, such as the surgical system of FIG. 1.

Referring also to FIG. 3, a surgical system 100 can include a control system 300 that can control operations of the equipment of the surgical system 100. The control system 300 can control the equipment to direct the manual repositioning of the surgical manipulator assembly 104. The control system 300 can also control the surgical manipulator assembly 104, e.g., joints of the remotely controllable arm 106 of the surgical manipulator assembly 104, to maintain the position and/or orientation of the distal portion 159 (or an item supported by the remotely controllable arm such as a cannula 150 or a surgical tool 134) during the manual repositioning. The control system 300 includes a processor 302, the surgical manipulator assembly 104, and a positioning indicator system 304. The control system 300 also optionally includes the surgeon's console 114, the electronics cart 116, and a sensor system 306.

The processor 302 can be one of several processors. Each of the surgeon's console 114, the surgical manipulator assembly 104, the electronics cart 116, and a positioning indicator system 304 of the control system 300 can include independent processors for controlling operations. A wired or wireless connection can enable communication between the surgical manipulator assembly 104, the electronics cart 116, the surgeon's console 114, and the positioning indicator system 304. The connection can be, for example, an optical fiber communication link between the surgeon's console 114, the electronics cart 116, and the surgical manipulator assembly 104. The control system 300, in some examples, can include a single processor that serves as a central electronic data processing unit capable of performing some or all of the data processing used to operate the surgical system 100.

The surgical system 100 can include sensors part of the sensor system 306 to detect treatment parameters and conditions of equipment in the surgical system. The surgical manipulator assembly 104 can include pose sensors 308 positioned at, for example, the joints 142b-142c and 148a-148g to detect relative poses of links along the surgical manipulator assembly 104. The pose sensors 308 can include a combination of pressure sensors, torque sensors, force sensors, position sensors, velocity sensors, accelerometers, rotary encoders, linear encoders, and other appropriate sensors to determine position and orientation of links and joints in the surgical manipulator assembly 104.

The pose sensors 308 can generate signals indicative of relative positions, relative orientations, or both relative positions and orientations of the setup assembly 109, the base 108, the remotely controllable arm 106, and one or more of the joints 142a-142c and 148a-148g. These pose sensors 308 optionally detect a pose of the remotely controllable arm 106 relative to a pose of the base 108, detect a pose of one link relative to another link, detect a pose of the surgical tool 134, or detect a pose of another element of the surgical manipulator assembly 104. These poses may be referenced to any appropriate reference; example references include the surgical environment 10, the floor surface, the patient 102, the base 108. For a given joint with a pose sensor, the pose sensor can detect a joint state of the joint. The sensor can detect the position and velocity of the joint within the available range of joint states and joint velocities for a given position of the distal portion 159 (or an item supported by the remotely controllable arm such as a cannula 150 or a surgical tool 134). The sensor can also detect relative link poses of the links connected at the given joint. This sensor can thereby detect the pose of the link within the range of link states available at the given pose of the distal portion 159 (or an item supported by the remotely controllable arm such as a cannula 150 or a surgical tool 134).

The pose sensors 308 optionally include a sensor that can detect a pose of the base 108 within the surgical environment 10. The sensor can generate signals that can be used by the processor 302 to compute the pose of the base 108 based on movement of the setup assembly 109 supporting the base 108 and enabling the base 108 to be moved about the surgical environment 10. The setup assembly 109 is, for example, supported within the surgical environment above the floor surface 20 on the wheels 136 of the cart 111. The wheels 136 may be operable with rotary encoders that can be used to track the horizontal position and orientation of the cart 111 on the floor surface 20 of the surgical environment 10. The horizontal position and orientation of the base 108 can then be determined from the horizontal position and orientation of the cart 111. The cart 111 of the setup assembly 109 alternatively or additionally includes an optical sensor that can track motion, e.g., position, velocity, orientation, and/or acceleration, of the cart 111 along the floor surface 20. The optical sensor, for example, is similar to that used in an optical mouse. The optical sensor captures images of the floor surface 20 as the cart 111 moves along the floor surface 20. The images of the floor surface 20 vary with the movement of the cart 111. The processor 302, using the captured images, can determine a position and orientation of the cart 111.

In some examples, the powered joints of the remotely controllable arm 106 can be manually repositioned by an operator. In some cases, the powered joints are manually positionable by an operator. A sensor associated with a powered joint can detect an external force that would cause articulation of the powered joint. In response to the detection of the external force, the processor 302 of the control system 300 can actuate the actuator associated with the powered joint such that the powered joint moves in the direction of the external force. The processor 302 may counteract external forces below an appropriate threshold for the sensor, but may treat external articulations exceeding the threshold as an input into the remotely controllable arm 106.

In some examples, the processor 302 can determine the position of the distal portion 159 (or an item supported by the remotely controllable arm 106 such as a cannula 150 or a surgical tool 134) directly by sensing motion of the remotely controllable arm 106 or the surgical tool 134. In some examples, the processor 302 can use forward kinematics to compute the motion. Using actual joint motion information from the pose sensors 308, e.g., data indicative of the joint states of the joints of the controllable arm 106, the processor 302 can determine a pose of the distal portion 159 (or an item supported by the remotely controllable arm such as a cannula 150 or a surgical tool 134). Joint torques, forces, velocities, orientations, and/or positions optionally are transmitted to the processor 302 such that the processor 302 can determine the motion of the distal portion 159 (or an item supported by the remotely controllable arm such as a cannula 150 or a surgical tool 134). Using forward kinematics, the processor 302 can use the information from the pose sensors 308 to compute the pose of the distal portion 159 (or an item supported by the remotely controllable arm such as a cannula 150 or a surgical tool 134) relative to the base 108. In some examples, if the remote center of motion and the reference point 162 correspond to a position along the cannula 150 or a surgical tool 134, particularly, the point along the cannula 150 or the surgical tool 134 in which such component is inserted into the access port on the patient 102, the processor 302 can determine the location of the reference point 162 and the remote center of motion based on the information from the pose sensors 308.

The sensor system 306 optionally includes a patient motion sensor 310 to measure motion of the patient 102 relative to the distal portion 159 (or an item supported by the remotely controllable arm such as a cannula 150 or a surgical tool 134). The patient motion sensor 310 can include a sensor proximate to the distal portion 159 that detects when a body of the patient 102 moves relative to the sensor. The sensor is, for example, an emitter-receiver sensor that detects a distance of nearby objects. The sensor can be an optical time-of-flight sensor that emits infrared light and receives the reflected infrared light to determine the distance of the patient 102. Relative changes in the distance over time can be indicative of patient motion.

The sensor system 306 alternatively or additionally includes a tool sensor 312 positioned such that the tool sensor 312 generates a sensor signal indicative of the force applied by the surgical tool 134 or cannula 150 on the patient 102 or vice versa. The tool sensor 312 can be positioned on the surgical tool 134 or cannula 150 to directly measure the applied force. In some examples, the tool sensor 312 is positioned at a joint, e.g., the joint 148g, to measure a torque. The processor 302 can then compute the applied force based on the torque at the joint 148g.

In some implementations, the sensor system 306 can include obstacle detection sensors 314. The obstacle detection sensors 314 can be positioned at one or more locations in the surgical system 100 to detect imminent collision or contact with nearby obstacles in the surgical environment 10. The surgical manipulator assembly 104 and/or the remotely controllable arm 106 can include obstacle detection sensors 314 to detect when portions of the surgical manipulator assembly 104 and/or the remotely controllable arm 106 contact or nearly contact nearby obstacles. The obstacles can include other equipment of the surgical system 100, such as the operating table 123, the electronics cart 116, and the surgeon's console 114. The obstacles can also include operators within the surgical environment 10, such as the surgeon 122, the operator 112, and the assistants 124, 126. The obstacle detection sensors 314 can include contact sensors, proximity sensors, optical time-of-flight sensors, and other sensors appropriate for detecting contact with an obstacle or a distance of an obstacle. The obstacle detection sensors 314 can also include, for example, tape switches, flexible sensing arrays, individual force sensing resistors or force sensing resistor arrays, or passive capacitive sensing systems. Signals from the obstacle detection sensors 314 can be monitored by the processor 302 of the control system 300, and, in some cases, the processor 302 may issue an alert upon determining that contact or collision may be imminent.

The control system 300 includes the positioning indicator system 304, which directs manual repositioning of the base 108 of the remotely controllable arm 106. The processor 302 controls the positioning indicator system 304 to provide human-perceptible indications to an operator to move the base 108 toward the optimal base location envelope 110. The indications include, for example, one or more of a tactile, audible, or visual indication. The operator can manipulate the base 108 directly. As described with respect to FIG. 1, the positioning indicator system 304 can provide the visual indication 115 to the operator 112 to direct the operator to move the base 108 toward the optimal base location envelope 110.

Figure 2B:
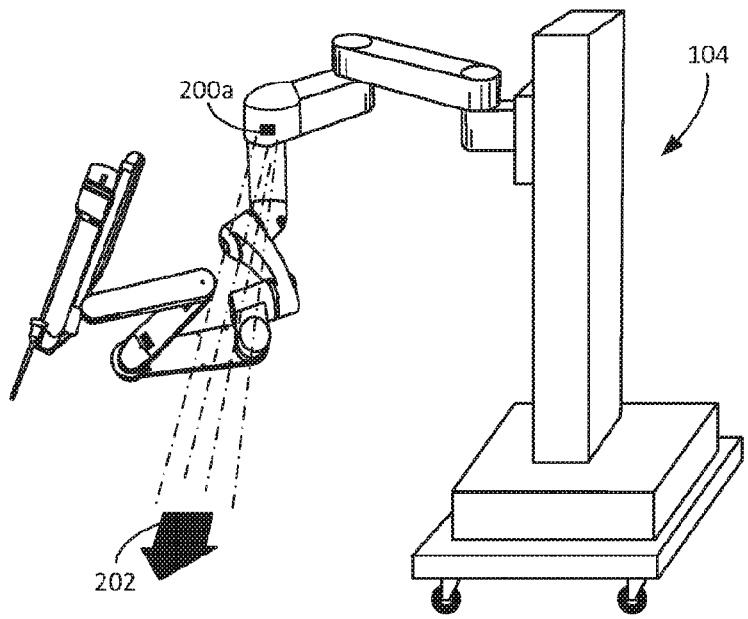
FIG. 2B is a perspective view of the surgical manipulator assembly of FIG. 2A with a first indicator light activated.
Figure 2C:
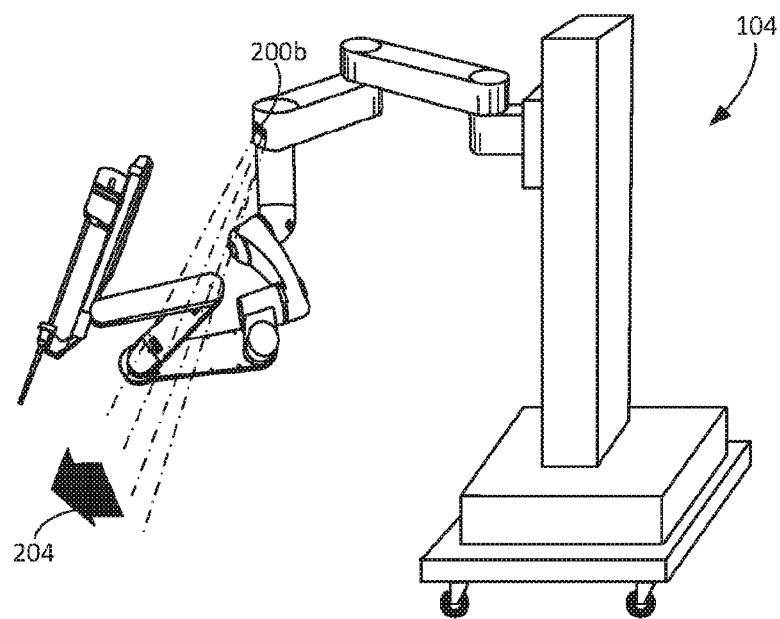
FIG. 2C is a perspective view of the surgical manipulator assembly of FIG. 2A with a second indicator light activated.

In the example shown in FIGS. 2B and 2C, the positioning indicator system 304 includes indicator lights 200a and 200b (collectively referred to as indicator lights 200) to provide visual indications to the operator 112. Each of the indicator lights 200 are positioned to indicate a different repositioning direction for the base 108 when the light is activated. In this regard, when a given indicator light is activated, the indicator light generates a visual indication in a given repositioning direction to guide the operator 112 to move the base 108 in the given repositioning direction. Selective activation of the indicator lights 200 can guide manual repositioning of the surgical manipulator assembly 104 to move the base 108 toward the optimal base location envelope 110 for the base 108 of the surgical manipulator assembly 104. For example, if the operator manually manipulates the base 108 directly, as the operator 112 moves the base 108, the indicator lights 200 are selectively activated to guide the operator to move the base 108 toward the optimal base location envelope 110.

The indicator lights 200 are optionally disposed on the base 108 of the surgical manipulator assembly 104. The indicator lights 200 can include, for example, four or more indicator lights. One of the indicator lights 200 can be illuminated to indicate to the operator that the surgical manipulator assembly 104 should be moved in the direction indicated by the illuminated indicator light. A combination of the indicator lights 200 can be illuminated to indicate to the operator that the surgical manipulator assembly 104 should be moved in a direction between the directions indicated by the indicator lights 200 when individually illuminated.

As shown in FIG. 2B, when the indicator light 200a is activated, the indicator light 200a projects light toward the floor surface 20 of the surgical environment 10. The light is projected in a first direction 202, thereby indicating to the operator 112 that base 108 of the surgical manipulator assembly 104 should be moved in the first direction 202 to be repositioned toward the optimal base location envelope 110. When the indicator light 200b is activated, as depicted in FIG. 2C, the indicator light 200b projects light toward the floor surface 20. The light is projected in a second direction 204, thereby indicating to the operator 112 that base 108 of the surgical manipulator assembly 104 should be moved in the second direction 204 to be repositioned toward the optimal base location envelope 110.

In some examples, the operator can move other portions of the surgical manipulator assembly 104 to move the base 108 toward the optimal base location envelope 110. For example, the operator can move parts of the setup assembly 109 to move the base 108 toward the optimal base location envelope 110. In this regard, in some implementations, the positioning indicator system 304 can also direct the manual repositioning of the links, joints, or other elements of the setup assembly 109 toward optimal locations, or direct the manual repositioning of these elements such that the base 108 is moved toward the optimal base location envelope 110. For example, the positioning indicator system 304 can include indicator lights to direct the manual repositioning of the cart 111 on the floor surface 20. Alternatively or additionally, the positioning indicator system 304 includes indicator lights to direct the manual repositioning of the links or joints of the setup arm 128.

Example System Operation

As described herein, the control system 300 for the surgical system 100 can guide the operator 112 as the operator 112 manually repositions the base 108. For example, before the surgery is performed, the operator 112 can perform the manual repositioning of the base 108 by manually moving the base 108 toward the optimal base location envelope 110 near or adjacent the operating table 123. The processor 302 controls the positioning indicator system 304 to direct the operator 112 as the operator 112 performs the manual repositioning.

During portions of the manual repositioning, the processor 302 directs the manual repositioning while controlling the remotely controllable arm 106 of the surgical manipulator assembly 104 to maintain the position and/or orientation of the distal portion 159 (or an item supported by the remotely controllable arm such as a cannula 150 or a surgical tool 134). The position and/or orientation may be maintained relative to a reference, such as reference point 162. Maintaining the position and/or orientation of relative to the reference point 162 can enable the operator to set the position of the distal portion 159 (or an item supported by the remotely controllable arm such as a cannula 150 or a surgical tool 134), e.g., near or at the access port on the patient 102, and then manually reposition the base 108 of the surgical manipulator assembly 104 without having to consider the position of the distal portion 159 (or an item supported by the remotely controllable arm such as a cannula 150 or a surgical tool 134). The operator 112 may move the base 108 during the manual repositioning without causing the position of the distal portion 159 (or an item supported by the remotely controllable arm such as a cannula 150 or a surgical tool 134) to shift. In this regard, the step of positioning the distal portion 159 (or an item supported by the remotely controllable arm such as a cannula 150 or a surgical tool 134) and the step of positioning the base 108 can be steps that are decoupled from one another such that they can be performed sequentially, without the results of one step affecting the outcome of the other step.

Figure 4:
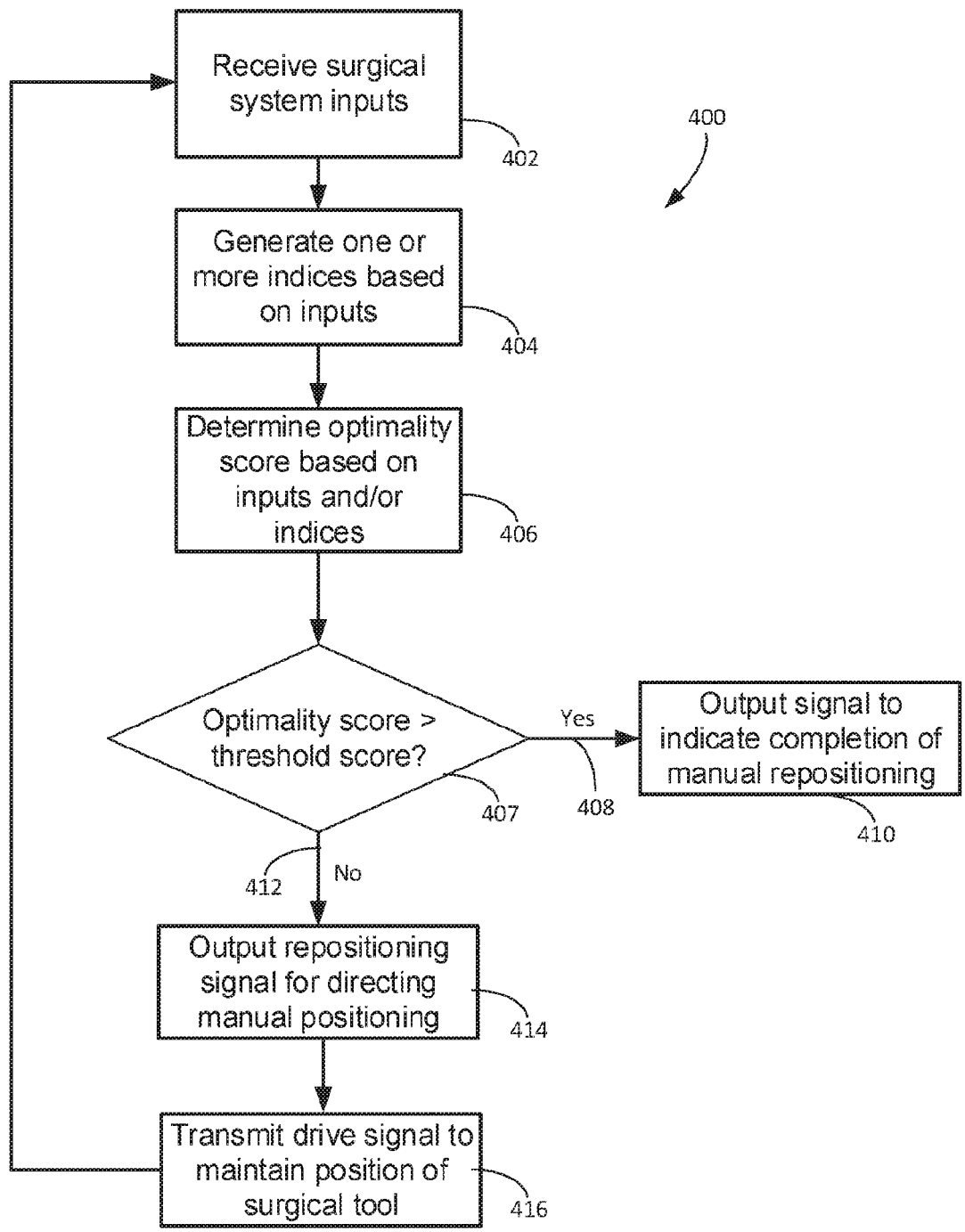
FIG. 4 is a flow chart of a process for directing a manual positioning of a base.
Figure 5:
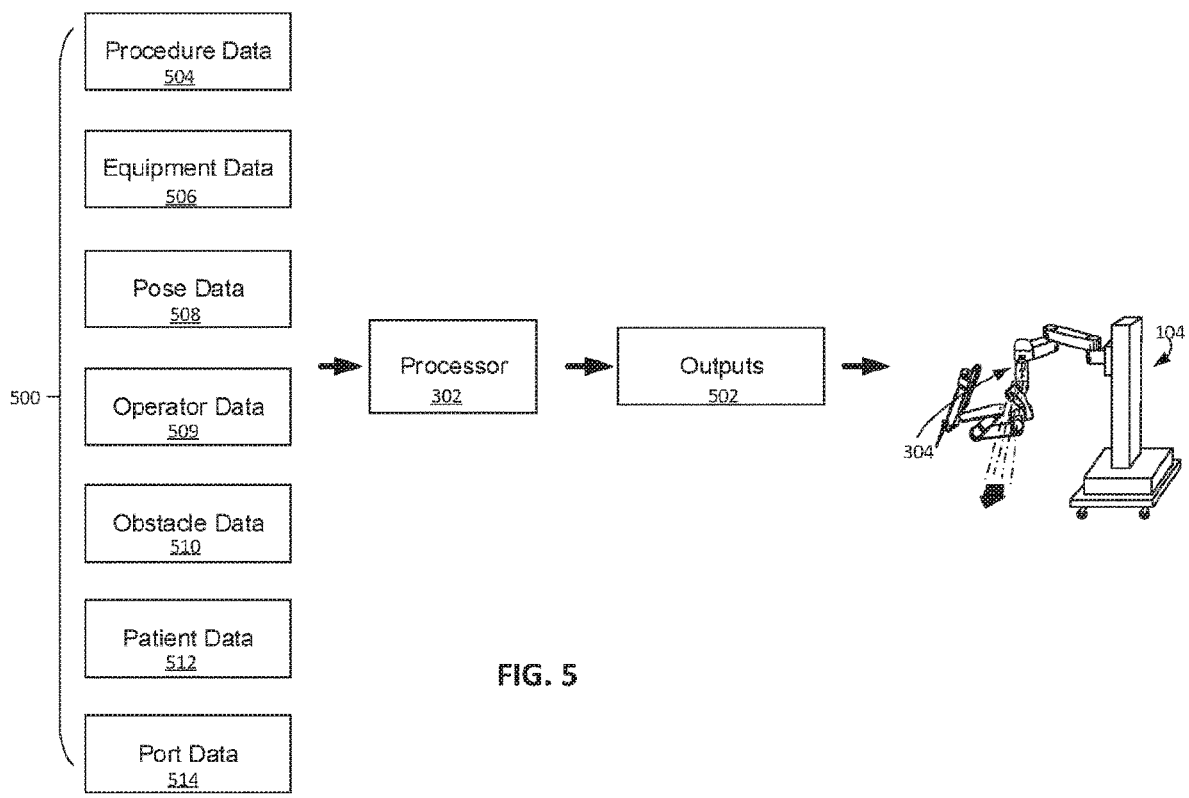
FIG. 5 is a diagram depicting inputs and outputs for a processor performing the process of FIG. 4.

Example processes and operations to direct the manual repositioning while the position and/or orientation of distal portion 159 (or an item supported by the remotely controllable arm such as a cannula 150 or a surgical tool 134) is maintained are described herein. FIG. 4, for instance, depicts a flow chart of a process 400 performed by the processor 302 to direct a manual repositioning of the base 108. FIG. 5 schematically depicts inputs and outputs used by the processor 302 to direct the manual repositioning of the base 108. Although the process 400 is described with respect to the surgical system 100 of FIG. 1, the process 400 is applicable to other implementations of surgical systems described herein.

At the start of the process 400, the processor 302 receives (operation 402) inputs from the surgical system 100. As shown in FIG. 5, the processor 302 can receive (operation 402) inputs 500 from the surgical system 100, which the processor 302 processes to determine outputs 502 to control the positioning indicator system 304, thereby directing the manual repositioning of the base 108. The inputs 500 can include user inputs specified by the operators as well as sensor signals generated by sensors of the sensor system 306. The inputs 500 can include, for example, procedure data 504, equipment data 506, pose data 508, operator data 509, obstacle data 510, patient data 512, and port data 514. The data 504, 506, 508-510, 512, 514 represent some examples of the data usable by the processor 302 to control the positioning indicator system 304 to direct the manual repositioning. Other types and contents of data may be appropriately used by the processor 302 to control the positioning indicator system 304.

The procedure data 504 include data indicative of the specific surgical procedure to be performed on the patient 102. The procedure data 504 can refer to specific requirements of a surgical workspace, e.g., an area around the patient 102 that the surgical tool 134 should be able to access during the surgery, due to the specific surgical procedure to be performed on the patient. A surgical procedure may require a predetermined extent of the workspace.

In some examples, a specific range of motion for the surgical tool 134 can be specified to represent the extent of the workspace. In some cases, the boundaries of the workspace can be delineated to represent the extent of the workspace. In some implementations, an operator can input the data indicative of the extent of workspace. The operator can input the data prior to the performing the procedure and prior to performing the manual repositioning of the base 108.

Before performing the manual repositioning of the base 108, an operator can demonstrate an extent of the workspace by moving the surgical tool 134 within an area representative of the workspace required or otherwise desired for the surgical tool 134 during the surgery. For example, an operator can move the surgical manipulator assembly 104 (with or without a tool being held) to indicate the workspace desired, or by moving a substitute of the surgical tool 134 to indicate the workspace desired. Example substitutes include a device that represents an average surgical tool that may be used during the procedure, a device that replicates a proximal portion of the surgical tool 134 but not the entire shaft and end effector, a device that projects a visual indication of locations associated with distal ends of surgical tools that may be used during the procedure, etc. Information about the desired range of motion of the remotely controllable arm 106 or the surgical tool 134 can be derived at least in part from such a demonstration. The pose sensors 308 of the sensor system 306, for example, can generate a signal indicative of a manual demonstration by the operator 112 of a desired workspace, and provide information about the desired range of motion of the remotely controllable arm 106. Sensors (e.g., the pose sensors 308) on the surgical manipulator assembly 104 can detect the physical movement of the surgical manipulator assembly 104 and/or the surgical tool 134) and generate signals indicative of the pose of the surgical manipulator assembly 104 and/or the surgical tool 134. As the surgical manipulator assembly 104 and/or the surgical tool 134 is moved, the processor 302 receives the procedure data 504 including these sensor signals and can then process these sensor signals to determine the extent of the workspace demonstrated by the operator.

The equipment data 506 include data indicative of specifications of the equipment to be used during the surgery. The equipment data 506 can include data that specifies a range of motion for each of the joints of the surgical manipulator assembly 104. The range of motion can be a structural or mechanical limitation.

For a given joint, the range of motion for the joint can refer to the amount of motion possible between two links connected by the joint. For a revolute joint, the equipment data 506 can specify a value for the range of motion that is between, for example, 90 degrees and 180 degrees (e.g., the range of motion of the joint is 90 degrees, 135 degrees, or 180 degrees). For a prismatic joint, the equipment data 506 can specify a value for the range of motion that is between, for example, 10 centimeters and 30 centimeters (e.g., the range of motion of the joint is 10 centimeters, 20 centimeters, or 30 centimeters). Other ranges of motion beyond those specified herein may be appropriate depending on the configuration of the remotely controllable arm 106 and the setup assembly 109. The ranges of motion indicated in the equipment data 506 can include ranges of motion for passive joints, active joints, or both.

The equipment data 506 can further indicate the structure of the remotely controllable arm 106 and the setup assembly 109. For example, the equipment data 506 can specify the number of joints, the types of each joint, the length of links of the remotely controllable arm 106, and other parameters pertaining to the structure of the remotely controllable arm 106.

The equipment data 506 can also include information pertaining to the type of the surgical tool 134 mounted to the remotely controllable arm 106. The type of the surgical tool 134 may affect, for example, an extent of the workspace and an amount of torque necessary to perform an operation. The type of the surgical tool 134 can be manually inputted by an operator. In some examples, the surgical tool 134 may include a detectable tag that indicates the type of the surgical tool 134.

The equipment data 506 can also include information regarding the operating table such as manufacturer and model; size and dimensions; range of motion, if the table top is moveable with respect to the table base; table rail dimensions; attachment locations and dimensions of detachable table segments, if any.

The pose data 508 include data indicative of poses of the joints, links, the surgical tool, and other components of the surgical manipulator assembly 104. The pose data 508 includes the initial pose of each of the joints and/or links of the remotely controllable arm 106, the initial pose of each of the joints and/or links of the setup assembly 109, the initial pose of the distal portion and/or the surgical tool 134, and the initial pose of the base 108. As the base 108 is moved during the manual repositioning, the pose sensors 308 can generate signals responsive to motion of the base 108. Based on the signals from the pose sensors 308, the processor 302 can control the remotely controllable arm 106 to maintain the position of the distal portion (or an item supported by the remotely controllable arm such as a cannula 150 or a surgical tool 134). The position and/or orientation may be maintained relative to a reference. Example references include the surgical environment 10, an anatomy of the patient 102, a reference point such as the reference point 162, a reference frame originating from reference point 162, etc.

The operator data 509 includes data pertaining to the surgical team, e.g., the operators, carrying out the surgical procedure. The operator data 509 includes, for example, information related to the capabilities, preferences for surgical equipment layout, levels of experience, levels of skill, and other operator-specific attributes. In some examples, an operator profile is created for each of the operators before the surgical procedure. A surgical team profile alternatively or additionally is created for a particular surgical team.

The obstacle data 510 include data indicative of poses or positions of the patient 102 and obstacles in the surgical environment 10 relative to the surgical manipulator assembly 104. In some examples, the obstacle data 510 can include a map of the surgical environment 10 inputted by the operator. The map can include locations of potential obstacles within the surgical environment 10, such as other pieces of equipment of the surgical system 100. The obstacle data 510 alternatively or additionally includes data from the obstacle detection sensors 314. As the remotely controllable arm 106, the setup assembly 109, and the base 108 are moved within the surgical environment 10, the obstacle detection sensors 314 can generate signals indicative of positions, orientations, or poses of obstacles within the surgical environment 10.

The patient data 512 include data indicative of patient-specific characteristics. The patient data 512 can include data indicative of patient habitus and patient geometry. In some examples, the operator inputs the patient habitus and the patient geometry. In some cases, an imaging device can produce images that can be analyzed by the processor 302 to determine the patient habitus and the patient geometry. The imaging device may be inserted into the patient 102 before the manual repositioning of the base 108 occurs. The endoscope can produce images usable for estimating the patient habitus and the patient geometry. In some examples, the patient data 512 can also include data indicative of the pose of the patient 102 relative to the remotely controllable arm 106 and/or the pose of the operating table 123 relative to the remotely controllable arm 106. The patient data 512 can include pre-operative images, such as x-ray images, x-ray computed tomography images, magnetic resonance imaging scans, and the like. In some cases, the patient data 512 includes intraoperative images or surface scans.

The port data 514 include data indicative of characteristics of the access port on the patient 102. The port data 514 can indicate a position and orientation of the access port. The processor 302 can use the port data 514 to determine the reference point 162 during the manual repositioning of the base 108. In some implementations, the port data 514 is based on a pose of the controllable arm 106 when a cannula is docked, when an operator indicates readiness for repositioning of the base, when a surgical tool is mounted, etc. In some implementations, a component such as a cannula 150 or a surgical tool 134 is inserted through the access port on the patient 102, and the processor 302 can determine the position and orientation of the access port based on signals from sensors on the remotely controllable arm 106.

In some examples, the port data 514 can be inputted by the operator. If the surgical tool 134 is not inserted into the access port before the manual repositioning of the base 108 occurs, the processor 302 can select the reference point 162 based on the inputted port data 514. The reference point 162 is selected such that the surgical tool 134 can be positioned and oriented to be easily inserted into the access port after the manual repositioning is complete. In particular, the surgical tool 134 can be in a retracted position during the manual repositioning and then translated axially to an insertion position such that the reference point 162 corresponds to the position of the access port.

After receiving (operation 402) the inputs, the processor 302 optionally generates (operation 404) one or more indices based on the inputs. The processor 302 can compute functions that each represent one of the indices. One or more of the indices can be selected, e.g., by the operator or in accordance to a default setting, to be optimized by the processor 302. The processor 302 can then optimize the functions of the selected indices, as described in greater detail with respect to operation 406.

Each of the indices generated at the operation 404 can represent an optimization goal for the processor 302. The indices can refer to values to be optimized during the manual repositioning of the base 108. Each index generated by the processor 302 during the operation 404 can be a value based on one or more of the inputs. The number of indices generated may depend on the number of degrees of freedom, in particular, the number of redundant degrees of freedom. In this regard, the indices generated at the operation 404 represent the indices for the current configuration of the surgical manipulator assembly 104 during the manual repositioning. The values for the indices may change as the base 108 is manually repositioned and the joints are moved during the manual repositioning.

Based on the inputs and/or the one or more indices, the processor 302 determines (operation 406) an optimum pose and an optimality score for the current pose of the base 108. The processor 302 can determine a range of optimum poses or optimum positions for the base 108 of the surgical manipulator assembly 104. The range of optimum poses or optimum positions can be represented as the optimal base location envelope 110. The optimal base location envelope 110 can correspond to a range of three-dimensional positions and orientations considered optimal for the base 108. In some implementations, the optimal base location envelope 110 corresponds to a range of optimal two-dimensional positions along a plane parallel to the floor surface. In some examples, the optimal base location envelope 110 includes multiple optimal positions having a maximum optimality score. The processor 302 can compute the optimal pose, the optimum poses, and/or the optimal base location envelope 110 based on the inputs 500. The processor 302 can generate functions for the values of the indices at the operations 404 and execute optimization strategies that use the functions to optimize each of the indices. The optimization strategies include, for example, a gradient descent-based optimization strategy, a least squares-based optimization strategy, or other appropriate strategies. The processor 302 can compute a solution to the functions in which the solution represents the optimal base pose or the optimal range of poses for the base 108 using the given optimization strategies. The optimization strategies enable the processor 302 to compute an optimality score representing the optimality of the current pose of the base 108. In some examples, the optimality score represents a proximity of the current pose of the base 108 to the optimal base pose or the optimal base location envelope 110.

In some examples, the processor 302 selects a single index as a primary goal and then computes a solution using the optimization strategies to optimize the index. When this solution calculated the processor 302 is under-constrained, the solution provided by the processor 302 may represent a subset of states available for the remotely controllable arm 106. To identify the specific commands to be transmitted to the joints of the remotely controllable arm 106 when a primary solution is under-constrained, the processor 302 can include a module that acts as a subspace filter to select a desired state of the remotely controllable arm 106 from among the subset of states. The subspace filter can also select a set of commands for the joints of the remotely controllable arm 106 to move the joints such that the remotely controllable arm 106 is placed in the desired state. Advantageously, the selected commands can be used to serve a second goal, e.g., to optimize a second index. In some examples, multiple indices are selected, and a weight is assigned to each of the selected indices. The weight is indicative of a priority of that index relative to other selected indices. For example, operators may determine that the procedure type and patient characteristics have greater priority for optimization than operator preference. Examples of optimization of multiple goals are described in the '229 patent, the entirety of which is incorporated herein by reference.

Each index may have a range of values considered to be optimal. When the index is within the optimal range of values, the remotely controllable arm 106 and the surgical tool 134 are in states beneficial to the operation of the surgical manipulator assembly 104 as compared to states of the remotely controllable arm 106 and the surgical tool 134 when the index is not within the optimal range of values. The optimal range of values for an index can correspond to any value of the index above a threshold value. The threshold value can be programmed as a default value, a percentage of a maximum or minimum value of the index, or can be inputted by the operator.

Various indices are described herein. These indices may be functions of one or more of the inputs 500. The example uses of combinations of the data 504, 506, 508, 510, 512, 514 described herein to compute the indices are not intended to be limiting. For a given implementation of the process 400, the processor 302 may generate one or more of the indices. In some implementations, the processor 302 does not generate indices, but rather, directs manual repositioning by directly comparing one or more of the inputs 500 to compute the optimality score.

The processor 302 optionally generates and optimizes a range of motion index based on the range of motion available for each of the joints. The range of motion index may be computed based on, for example, the equipment data 506 and the pose data 508. For example, for a revolute joint that can rotate in two directions about an axis, the processor 302 can determine an amount of motion available in each of the two directions. The processor 302 can determine a target range of joint states for each of the joints of the remotely controllable arm 106. In some cases, it can be beneficial for the joint to be positioned such that the joint can move in both directions a substantially equal amount, whereas in some examples, it can be desirable to maximize the amount of motion available in a single direction. The target range of joint states thus can be a subset of the available range of joint states for a given joint. The processor 302 can compute the range of motion index by considering range of motion requirements for each of the joints of the remotely controllable arm 106.

The range of motion index alternatively or additionally considers the range of motion of the surgical tool 134. In particular, the processor 302 can compute the range of motion index based on whether the surgical tool 134 has sufficient range of motion to reach the relevant portions of the anatomy for the specific surgical procedure. In this regard, the processor 302 may also use procedure data 504 in computing the range of motion index.

As the remotely controllable arm 106 moves during the manual repositioning to maintain the position and/or orientation of the distal portion (or an item supported by the remotely controllable arm such as a cannula 150 or a surgical tool 134), the pose sensors 308 can generate signals responsive to motion of the joints and/or links of the remotely controllable arm 106, thereby updating the pose data 508. Upon receiving these signals, the processor 302 can update its determination of the range of motion index based on the new pose of each of the joints and/or links of the remotely controllable arm 106.

The processor 302 alternatively or additionally computes a smoothness index. The smoothness index is indicative of the motion performance of the surgical tool 134 and, in some cases, the motion performance of some or all of the joints of the remotely controllable arm 106. The processor 302 can estimate the motion performance by determining a resolution of motion of the surgical tool 134 that is possible for the current pose of the remotely controllable arm 106 and the surgical tool 134. For example, for a particular joint, actuation of the joint by an increment (e.g., a given applied voltage or current) may result in an amount of motion of the surgical tool 134 that depends on the pose of each of the joints of the remotely controllable arm 106 and the pose of the surgical tool 134. In some implementations, the smoothness index is computed based on the spatial resolution achievable as a function of pose and joint sensor position resolution. The smoothness index can account for the size of the motion caused by the increment (e.g., incremental voltage or current) applied. In this regard, a smaller motion of the surgical tool 134 from a given applied increment can result in improved motion performance of the surgical tool 134 and greater smoothness of motion. The processor 302 can compute the smoothness index based on, for example, the equipment data 506 and the pose data 508.

The processor 302 optionally computes a torque index for the surgical tool 134. The torque index can be indicative of a torque that the remotely controllable arm 106 can exert on the surgical tool 134. In some implementations, the surgical procedure may require that the remotely controllable arm 106 be able to manipulate the surgical tool 134 with a minimum torque necessary to perform the surgical procedure. It may be beneficial in these cases to maximize the torque achievable by the surgical tool 134. The achievable torque, however, can depend on the positions and orientations of the joints relative to the surgical tool 134. The processor 302 can compute the torque index based on, for example, the procedure data 504, the equipment data 506, and the pose data 508.

In some implementations, instead of or in addition to a torque index, a force index indicative of a force that the remotely controllable arm 106 can exert on the surgical tool 134 is computed. Furthermore, the torque index and/or the force index may account for forces and torques on joints of the surgical manipulator assembly 104 such that forces and/or torques on a particular joint can be minimized during motion of the remotely controllable arm 106 within the workspace.

The processor 302 can compute a workspace index representative of the portion of the workspace accessible by the surgical tool 134 for the current state of the remotely controllable arm 106. The processor 302 can compute the workspace index based on the workspace indicated in the procedure data 504, e.g., demonstrated by the operator. The positioning indicator system can be controlled by the processor 302 to direct the manual repositioning of the base 108 to optimize the workspace index. The processor can control the positioning indicator system based on the signals from the pose sensors 308 indicative of the manual demonstration and the data used to compute the workspace index.

The processor 302 can compute the portion of the workspace accessible by the surgical tool 134 based on the equipment data 506 and the pose data 508 by determining the extent that the surgical tool 134 can be moved given the ranges of motion of the joints of the remotely controllable arm 106. In some implementations, the processor 302 can use the patient data 512 to consider patient geometry and patient habitus in determining the workspace index. In some examples, the processor 302 can base the computation of the workspace index in part on the port data 514, in particular, on the location and orientation of the access port on the patient 102. In some examples, the patient data 512 includes images of the patient physiology that, when used in combination with the procedure data 504, can be used to estimate required instrument workspace bounds.

The processor 302, in some examples, computes a singularity index that indicates the likelihood that the joints of the remotely controllable arm 106 may be actuated to a state corresponding to a kinematic singularity. For example, for the remotely controllable arm 106, a kinematic singularity occurs when the remotely controllable arm 106 is in a state in which it loses its ability to move, or to apply forces, in one or more directions. The processor 302 can determine potential kinematic singularities based on the equipment data 506. For example, the kinematic singularities for the joints may depend on the present configuration of the remotely controllable arm 106.

The processor 302 optionally estimates an obstacle index based on the pose data 508 and the obstacle data 510. The obstacle index represents a likelihood that the remotely controllable arm 106 may collide with nearby obstacles. In this regard, using the obstacle data 510, the current pose of the remotely controllable arm 106, and the procedure data 504, the processor 302 can compute the obstacle index to determine whether the remotely controllable arm 106 may collide with a nearby obstacle if the surgical tool 134 is to be able to access the extent of the workspace specified in the procedure data 504.

The processor 302 alternatively or additionally computes a patient force index indicative of an amount of force exerted on the patient. For example, the patient force index may be computed based on the pose data 508, the patient data 512, and the port data 514 and may be indicative of an amount of torque or force that may be exerted on a wall of the patient 102 around the vicinity of the access port. The processor 302 can use the patient force index to determine if the remotely controllable arm 106 or the base 108 are being moved in a manner that may place force exceeding a desired amount on the tissue of the patient 102.

In some implementations, the processor 302 optionally computes a dexterity index that represents a dexterity of the surgical tool 134 in the given pose of the surgical tool 134.

The dexterity index can be an aggregate index that accounts for one or more of the smoothness index, the torque index, the workspace index, and the singularity avoidance index. In some implementations, the dexterity index is computed based on a manipulability index and/or a Jacobian condition number for the joints of the surgical manipulator assembly 104.

In some implementations, an optimization strategy for a surgical operation is based on data from previous surgical operations. The data from the previous surgical operations include, for example, inputs collected during the previous surgical operations, indices determined during the previous surgical operations, and/or scores determined during the previous surgical operations. In some cases, the optimization strategy is determined using a machine learning approach, such as, for example, artificial neural networks.

After the processor 302 determines (operation 406) the optimum base pose and the optimality score for the current pose, the processor 302 compares (operation 407) the optimality score to a threshold optimality score. Whether the optimality score is greater than (operation 408) or less than (operation 412) the threshold optimality score, the processor 302 can generate and deliver the outputs 502. As shown in FIG. 5, the outputs 502 can be transmitted to the surgical manipulator assembly 104 to control an operation of the surgical manipulator assembly 104.

If the optimality score is greater than a threshold optimality score (e.g., operation 408), the processor 302 optionally outputs (operation 410) a signal that activates an indicator signifying the manual repositioning is complete. If the base 108 includes the indicator lights 200, the signal indicating the completion of the manual repositioning can be illumination of each of the indicator lights 200 in a specific pattern or sequence. For example, the processor 302 can control the positioning indicator system 304 such that all of the indicator lights 200 are illuminated. In some examples, the processor 302 controls a speaker to provide audible signal indicating completion of the manual repositioning. In some implementations, the optimality score is maximized at operation 408. Alternatively or additionally, when the optimality score is maximized, the optimization results in minimizing a score, such as an error score.

In some examples, the positioning indicator system 304 is controlled to guide the movement of the base 108 such that the base 108 is within a range of positions above the threshold optimality score. For example, if the optimization process does not account for certain conditions important for the operator, e.g., heuristics related to the surgical operation that are not considered during the process 400, the positioning indicator system 304 provides the range of positions to provide flexibility for the operator in repositioning the base 108. The operator can select a position that may not have the maximum optimality score but that may fulfill other conditions that the process 400 does not consider in controlling the positioning indicator system 304.

If the optimality score is less than (operation 412) the threshold optimality score, the processor 302 outputs (operation 414) a repositioning signal to direct the manual repositioning. The processor 302 can transmit the repositioning signal to the positioning indicator system 304. In some examples, as shown in FIG. 5, the processor 302 transmits the signal to the surgical manipulator assembly 104, which includes the indicator lights 200 forming part of the positioning indicator system 304. The repositioning signal causes the indicator lights 200 to illuminate, thereby signifying a repositioning direction that the operator should move the base 108 of the surgical manipulator assembly 104 to reposition the base 108 toward the optimum base pose or toward the optimal base location envelope 110.

The processor 302 then transmits (operation 416) a drive signal to maintain a position and/or orientation of the distal portion (or an item supported by the remotely controllable arm such as a cannula 150 or a surgical tool 134) relative to a reference, such as the reference point 162. The processor 302 generates the drive signal based on signals from the sensors. For example, the pose data 508 may indicate that the base 108 is being moved in the repositioning direction, e.g., at a detected velocity and acceleration. The processor 302, in turn, can generate a drive signal that causes the joints to move in response to the movement of the base 108 such that the position and/or orientation of the distal portion (or an item supported by the remotely controllable arm such as a cannula 150 or a surgical tool 134) is maintained. The position and/or orientation may be maintained relative to a reference, such as the reference point 162.

In some examples, while outputting (operation 414) the repositioning signal or transmitting (operation 416) the drive signal, the processor 302 may activate brakes on the joints of the remotely controllable arm 106, activate a braking mechanism to stop movement of the base 108, activate a braking mechanism to stop movement of the setup assembly 109, and/or activate the braking mechanism associated with the wheels 136 on the cart 111 to stop movement of the cart 111. The processor 302 may control the brakes or braking mechanism based on changes in the value of the patient force index. For example, based on the patient force index, the processor 302 may determine that force exceeding a desired amount is being applied to the tissue of the patient 102. In this regard, the operator 112 may be repositioning the base 108 in a direction away from the optimal base location envelope 110, and the processor 302 may seek to inhibit this motion. In some implementations, the processor 302 is unable to drive the remotely controllable arm 106 to maintain the distal portion (or an item supported by the remotely controllable arm 106 such as a cannula 150 or a surgical tool 134) in its desired position and/or orientation with respect to a reference, such as a reference frame with its origin at the reference point 162. This may be due to, for example, a joint limit, singularity, excessive vibration, or excessive velocity/acceleration of the motion of the base 108.

Using the pose data 508, the processor 302 can determine or estimate a remote center of motion for the remotely controllable arm (which is often the same remote center of motion for a cannula or a surgical tool 134 coupled to the remotely controllable arm) and can control actuation of a powered joint of the remotely controllable arm 106 to maintain the remote center of motion. The processor 302 optionally uses inverse kinematics to determine how the joints should be driven to maintain the position and/or orientation of the distal portion (or an item supported by the remotely controllable arm such as a cannula 150 or a surgical tool 134). The actuator of the powered joint can be selectively driven to maintain the position and/or orientation of the distal portion (or an item supported by the remotely controllable arm such as a cannula 150 or a surgical tool 134) and/or to position the powered joint in a more optimal position. In some cases, the processor 302 controls the actuator of the powered joint to inhibit motion of the powered joint that may result due to the movement of the base 108. In some examples, the processor 302 controls the actuator of the powered joint to cause motion of the powered joint toward a more optimal position. Examples of such methods are described in the '229 patent incorporated herein by reference.

As described herein, the motion of the remotely controllable arm and/or surgical tool 134 can be constrained such that the surgical tool 134 rotates about a pivot point defined by the reference point 162. In estimating these pivot points, the processor 302 can selectively implement different modes characterized by a compliance or stiffness of the remotely controllable arm 106. The processor 302 can implement different modes over a range of compliance or stiffness for the pivot point or remote center of motion after an estimate pivot point is computed. The range can span between a pivot point being compliant, e.g., resulting in a passive pivot point, and a pivot point being stiff, e.g., resulting in a fixed pivot point.

For a fixed pivot point, the estimated pivot point can be compared to a desired pivot point to generate an error output that can be used to drive the pivot point of the remotely controllable arm (for example, of the distal portion of the remotely controllable arm) and/or the surgical tool 134 to the desired location. For a passive pivot point, the desired pivot location may not be a primary or overriding objective. The estimated pivot point can still be used for error detection. Changes in estimated pivot point locations may indicate that the patient 102 has been moved or that a sensor is malfunctioning, thereby giving the processor 302 an opportunity to take corrective action.

The processor 302 optionally allows the compliance or stiffness of the remotely controllable arm 106 to be changed throughout the range. For example, the joint 148g can be an instrument holder wrist joint enabling pivotal motion about two axes. When the joint 148g is controlled to be at the compliant end of the range, the processor 302 can move the proximal end of the surgical tool 134 in space while the actuators of the joint 148g apply little or no torque. In this regard, the surgical tool 134 acts as if it is coupled to the remotely controllable arm 106 by a pair of passive joints. In this mode, the interaction between the elongate shaft 152 and the tissue of the patient 102 along the access port induces the pivotal motion of the distal portion (or an item supported by the remotely controllable arm such as a cannula 150 or a surgical tool 134) about the pivot point.

When the joint 148g is controlled to be at the stiff end of the range, the processor 302 may determine the location of the access port from the port data 514 and use the location of the access port as an input indicative of the reference point 162 about which the distal portion (or an item supported by the remotely controllable arm such as a cannula 150 or a surgical tool 134) should rotate. In some cases, the processor 302 may calculate the location of the access port based on the pose data 508 and may treat the location of the access port as the reference point 162. The processor 302 may then drive actuators associated with each joint of the remotely controllable arm 106 disposed proximal of the pivot point such that any lateral force against the elongate shaft 152 at the calculate pivot point results in a reaction force to keep the elongate shaft 152 through the pivot point. The processor 302 thus may control the joints of the remotely controllable arm 106 such that the remotely controllable arm 106 behaves in a manner similar to mechanically constrained remote center linkages.

Implementations may fall between providing calculated motion about a pivot point corresponding to the access site and moving the remote center of motion within an acceptable range when the tissue along the access port moves without imposing excessive lateral forces on the tissue. The '229 patent—the entirety of which is incorporated herein by reference in its entirety—describes other examples of computing remote centers of motion and pivot points.

After the processor 302 outputs (operation 414) the repositioning signal and transmits (operation 416) the drive signal, the processor 302 can repeat the operations 402, 404, 406, 407, 412, 414, and 416 until the processor 302 determines that the optimality score of the base pose exceeds the threshold optimality score. At that point, the processor 302 can then perform operations 408 and 410 to indicate completion of the manual repositioning.

In some implementations, rather than repeating the operations 402, 404, 406, 407, 412, 414, and 416 until the processor 302 determines that the optimality score of the base pose exceeds the threshold optimality score, the manual repositioning of the base 108 is ceased before the optimality score exceeds the threshold optimality score. For example, the operator can provide a user input to override the process 400 and to cause the processor 302 to discontinue repetition of the operations to guide manual repositioning. Alternatively, the processor 302 can automatically cease guiding the manual repositioning of the base 108 in response to a predefined condition being satisfied. The predefined condition can indicate to the processor 302 that the base 108 is unable to be repositioned into the optimal base location envelope 110. For example, if the optimality score does not exceed the threshold optimality score after a predefined amount of time has elapsed after the process 400 is initiated, e.g., 5 to 15 minutes, the processor 302 overrides the process 400. In further examples, the processor 302 tracks a number of instances that the base 108 is moved in a direction away from the optimal base location envelope 110 and overrides the process 400 when the number of instances exceeds a predefined amount, e.g., 10 to 20 instances. In further examples, the processor 302 determines, based on the obstacle data 510, that there does not exist a path of movement for the base 108 into the optimal base location envelope 110 due to obstacles between the current location of the base 108 and the optimal base location envelope 110. If the manual repositioning of the base 108 is ceased before the optimality score exceeds the threshold optimality score, the processor 302 can issue an alert indicating that the base 108 is in a sub-optimal position, e.g., is outside of the optimal base location envelope 110.

Figure 6A:
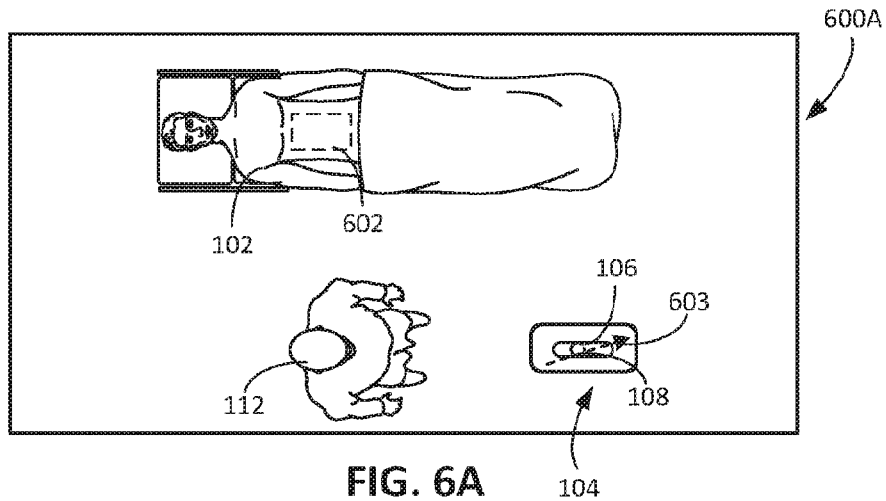
FIGS. 6A to 6P are top views depicting operations for positioning a surgical manipulator assembly adjacent an operating table.
Figure 6B:
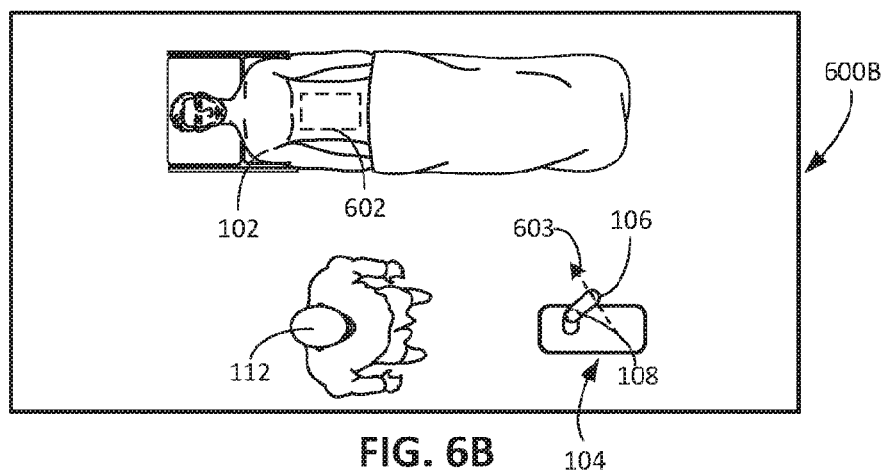
Figure 6C:
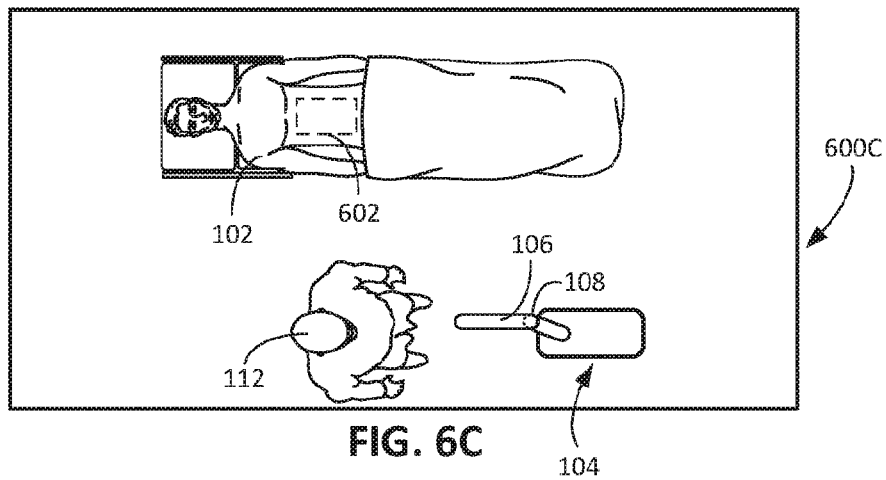
Figure 6D:
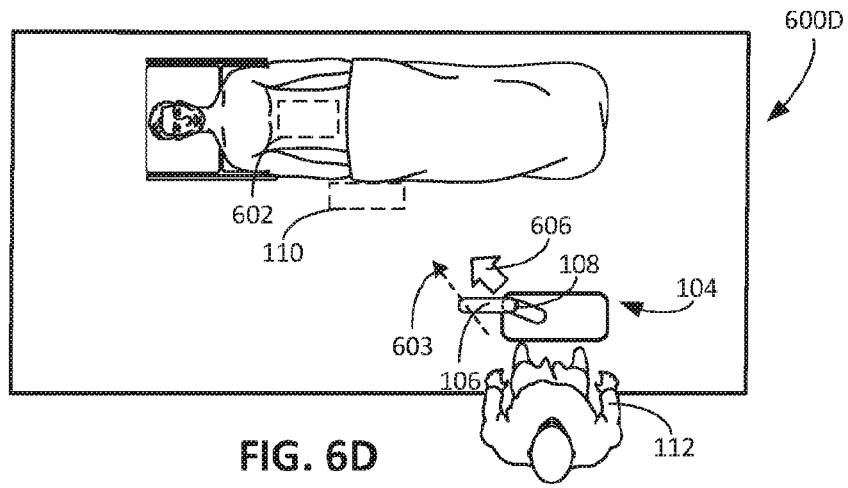
Figure 6E:
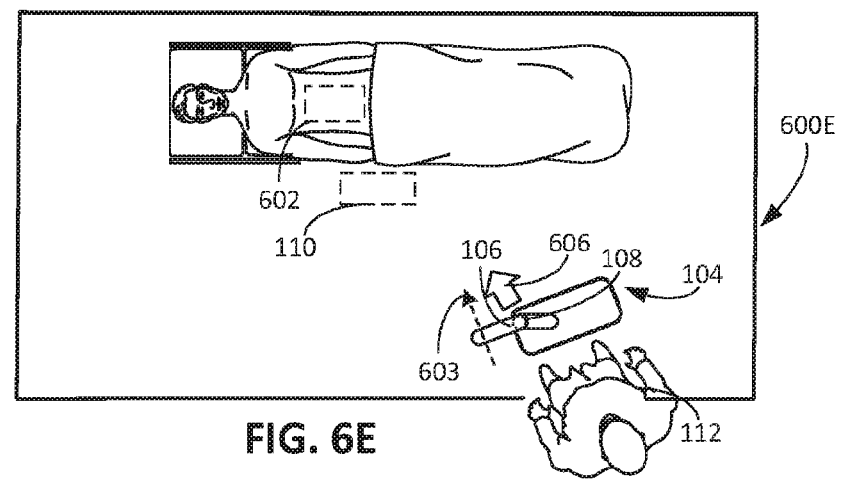
Figure 6F:
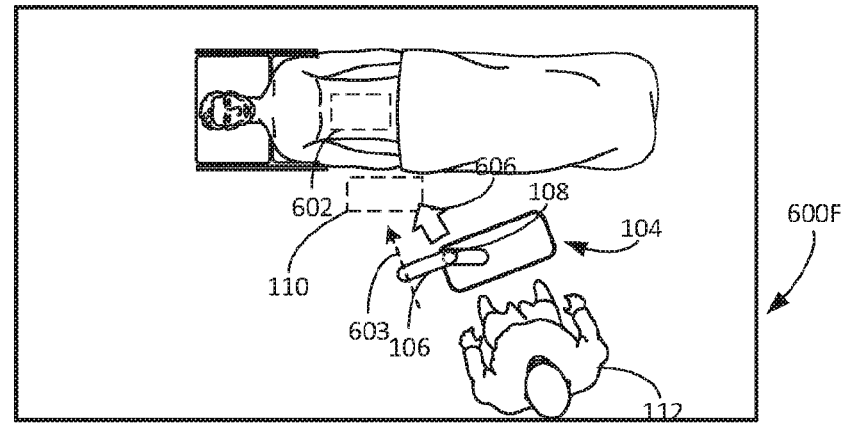
Figure 6G:
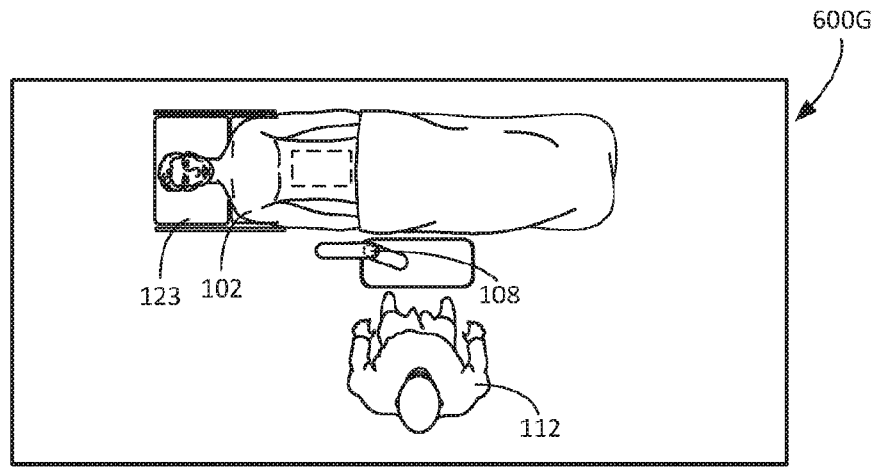
Figure 6H:
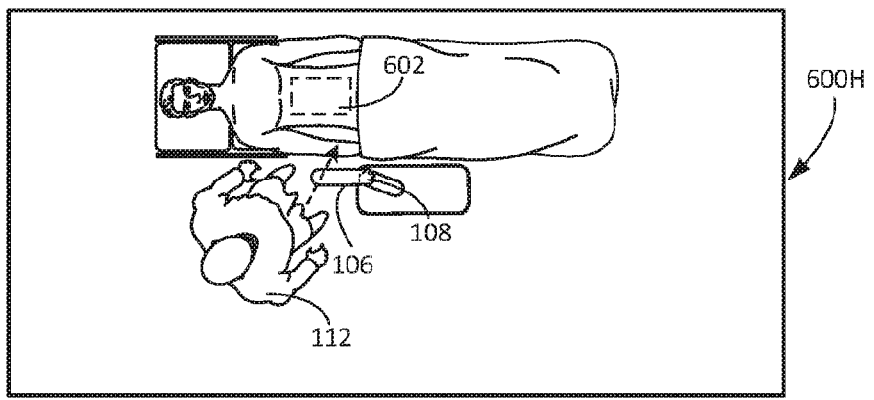
Figure 6I:
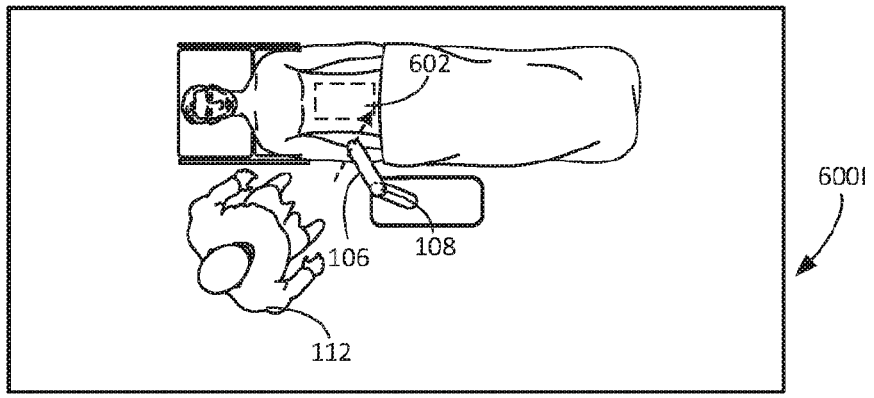
Figure 6J:
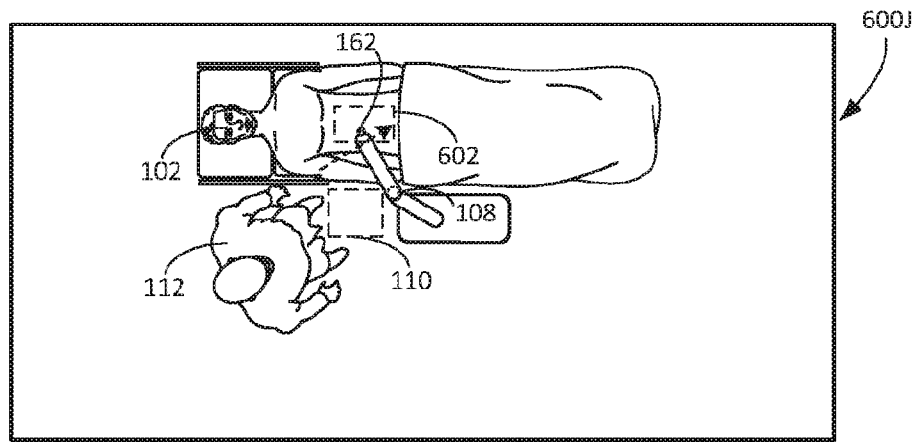
Figure 6K:
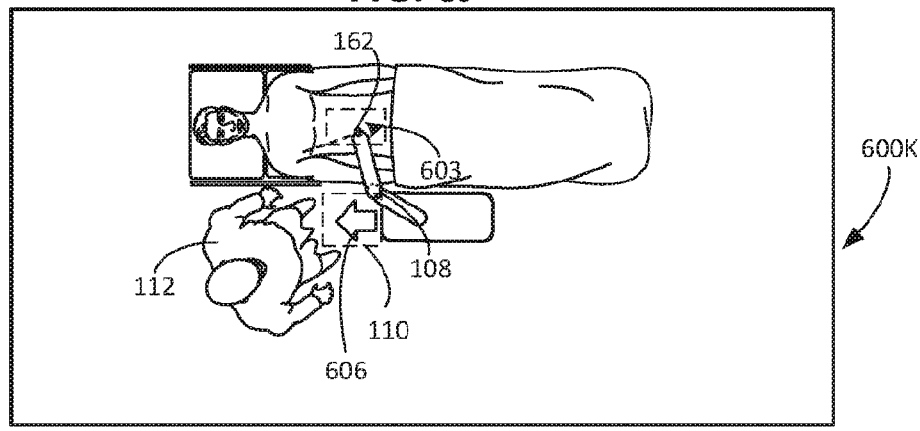
Figure 6L:
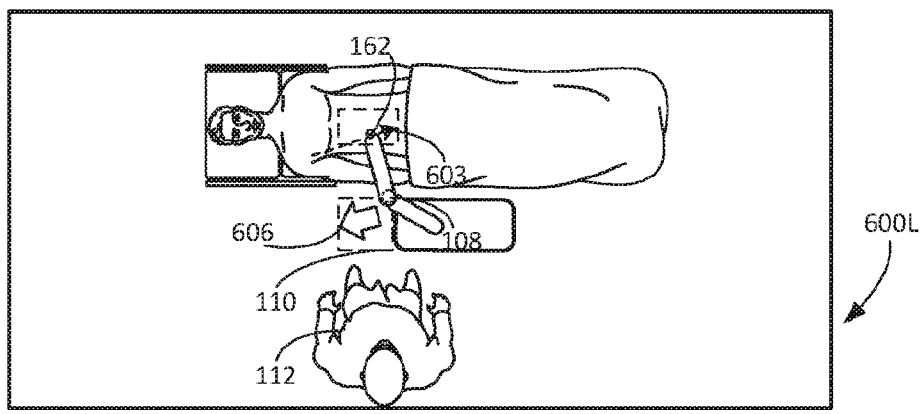
Figure 6M:
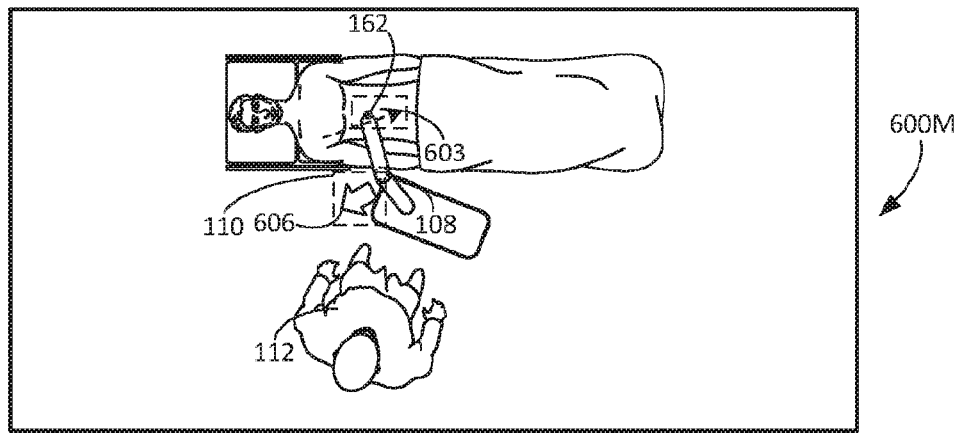
Figure 6N:
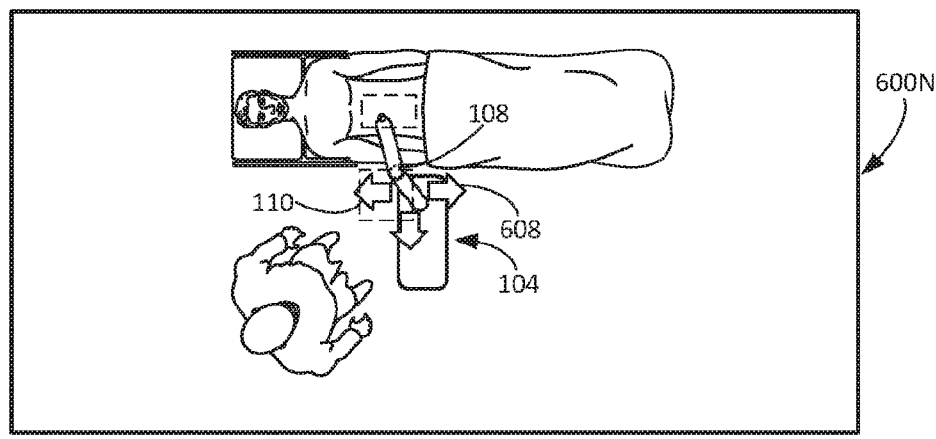
Figure 6O:
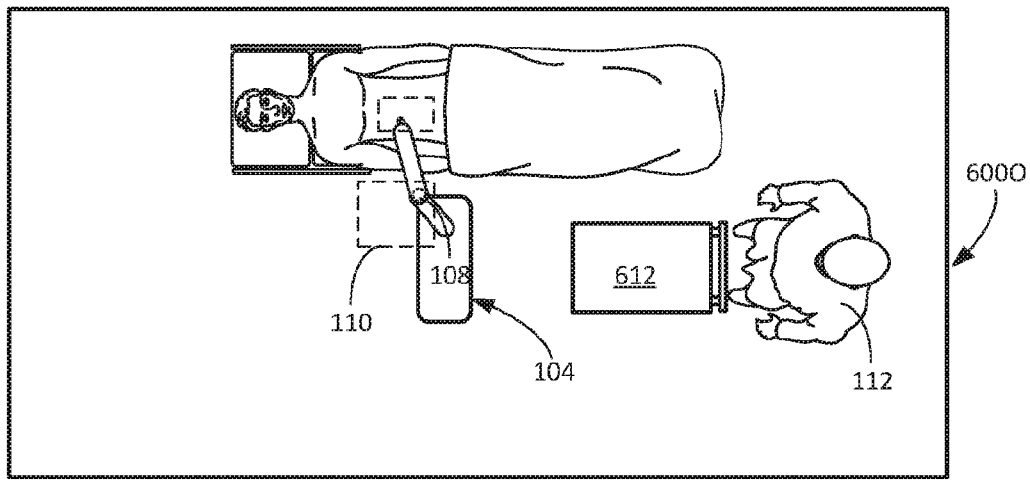
Figure 6P:
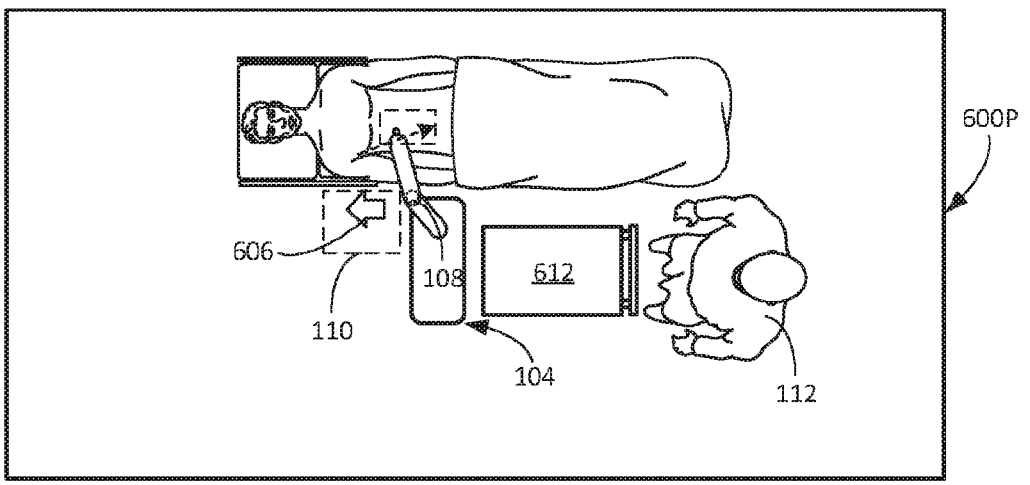

FIGS. 6A to 6P depict a sequence of operations 600A to 600P during which the operator 112 manually repositions the base 108 of the surgical manipulator assembly 104 adjacent to the operating table 123 supporting the patient 102 such that the surgical tool (not shown) mounted to the remotely controllable arm 106 can reach a workspace 602 around the patient 102. Each of the operations 600A to 600P can include sub-operations performed by the operator 112, a processor (e.g., the processor 302 of the control system 300), or a combination thereof. In some implementations, some or all of the operations 600A to 600P are performed by multiple operators.

In FIG. 6A, the surgical manipulator assembly 104 is positioned in the surgical environment 10. The remotely controllable arm 106 can be in a stowed configuration. The remotely controllable arm 106 can be controlled by the processor during operations 600A, 600B, and 600C to deploy the remotely controllable arm 106. The processor can control joints of the remotely controllable arm 106 such that the remotely controllable arm 106 extends further from the base 108, as shown in operations 600B and 600C of FIGS. 6B and 6C, respectively. The processor can actuate the joints such that the distal portion (or an item supported by the remotely controllable arm 106 such as a cannula 150 or a surgical tool at a distal link of the remotely controllable arm 106) is moved in a deployment direction 603. In some examples, instead of the processor controlling the joints to move the remotely controllable arm 106, the operator manually moves the remotely controllable arm 106 into the deployed position shown in FIG. 6C. When the remotely controllable arm 106 is deployed, the operator 112 can cover the remotely controllable arm 106 with a sterile drape (not shown).

In FIGS. 6D to 6F, respectively, the operator 112 manually repositions the base 108 such that the surgical manipulator assembly 104 is positioned adjacent the workspace 602. In some examples, during operations 600D to 600F, the processor can control a positioning indicator system (e.g., the positioning indicator system 304) to provide an indication of a repositioning direction 606 that the operator 112 should push the base 108. The indicator can be a visual indicator projected on the floor surface. In some examples, the processor can compute the optimal base location or the optimal base location envelope 110 and then control the positioning indicator system to indicate a repositioning direction 606 that would direct the operator 112 to move the base 108 toward the optimal base location envelope 110. In some implementations, inertia of the remotely controllable arm 106 and the base 108 may cause the remotely controllable arm 106 to move relative to the base 108 while the operator 112 moves the base 108 toward the optimal base location envelope 110. While the operator 112 moves the base 108, the processor can control joints of the remotely controllable arm 106 such that the remotely controllable arm 106 remains in the deployed position. In this regard, the joints may be driven in the deployment direction 603 shown in each of FIGS. 6D to 6F during the operations 600D to 600F.

At operation 600G shown in FIG. 6G, the base 108 is positioned adjacent to the operating table 123 and the patient 102. At operation 600H, 600I, and 600J shown in FIGS. 6H, 6I, and 6J, respectively, the remotely controllable arm 106 is then deployed such that the surgical tool would be within the workspace 602 when mounted on the remotely controllable arm 106. The deployment of the remotely controllable arm 106 can be controlled by the processor, e.g., through actuation of joints of the remotely controllable arm 106, or the operator 112 can manually deploy the remotely controllable arm 106.

When the remotely controllable arm 106 is deployed, in some implementations, the operator 112 can demonstrate the extent of the workspace 602. The operator 112 can, for example, manually manipulate the instrument holder or other portions of the remotely controllable arm 106 so that a portion of the remotely controllable arm 106 (or the surgical tool if mounted to the remotely controllable arm 106) is moved through the boundaries of the workspace 602. The processor can then receive the sensor signals from pose sensors on the remotely controllable arm 106 and then use those signals to estimate the extent of the workspace 602. Other methods of demonstrating the workspace 602 are described herein.

At operation 600J, the reference is specified. In this example, the reference is a reference point 162. In some examples, at operation 600J, the surgical tool is inserted into an access port on the patient 102, and the reference point is defined to correspond to a location of the access port. The operator 112 can clutch various joints of the remotely controllable arm 106 to manipulate the distal link or other portion(s) of the remotely controllable arm 106 to insert the surgical tool into the access port. Examples of clutching are described in detail in the '223 patent incorporated herein by reference.

In some implementations, a position for defining the reference is provided to the processor in a manner other than by physically placing the surgical tool through the access port. The processor can determine the reference point 162 such that the surgical tool can be inserted into the access port after the manual repositioning of the base 108 is complete. The reference point 162 can be a point on a component in physical contact with the remotely controllable arm 106, or a point in space that is not mechanically connected or part of a component mechanically connected to the remotely controllable arm 106. For example, if the instrument holder 132 is coupled to the cannula 150 and the cannula 150 is inserted into the patient, the reference point 162 can refer to a point along the cannula 150, such as where the cannula 150 contacts a body wall of the patient. If the instrument holder 132 is decoupled from the cannula 150, the reference point 162 can refer to a point associated with where an installed cannula would be if installed, in the surgical environment 10 that is not mechanically connected to the remotely controllable arm 106. The reference point 162 may be indicated in other ways in various implementations. In some implementations, the operator manipulates an input device to indicate that the remotely controllable arm 106 is proximate to the access port on the patient 102, the remotely controllable arm 106 is docked to a cannula already inserted into an access port on the patient 102, a cannula held by the remotely controllable arm 106 is inserted into the patient 102, image acquisition and recognition is performed to identify incisions in the patient or guide markings placed on the patient for indicating reference point(s) and/or direction(s), etc.

At operation 600J, the processor can determine the optimal base location envelope 110 based on received inputs, as described in greater detail with respect to FIGS. 4 and 5. As shown in FIGS. 6K to 6M, at operations 600K to 600M, respectively, the processor then guides the manual repositioning of the base 108. The processor controls the positioning indicator system to indicate a repositioning direction 606 for the base 108. The repositioning direction 606 indicates the direction that the operator 112 should reposition the base 108 such that the base 108 is moved toward the optimal base location envelope 110. The operator 112, in accordance to the repositioning direction 606 provided by the positioning indicator system, manually repositions the base 108. While the operator 112 manually repositions the base 108, as described with respect to FIGS. 4 and 5, the processor can detect motion of the base 108 and control actuation of the joints of the remotely controllable arm 106 such that the position and/or orientation of the distal portion (or an item supported by the remotely controllable arm 106 such as a cannula 150 or a surgical tool) is maintained relative to a reference (e.g. the reference point 162) during the manual repositioning. The processor can thus cause one or more portions of the remotely controllable arm 106 (e.g. the distal end or other portion(s)) of the remotely controllable arm 106) to move relative to the base 108 in the deployment direction 603 while the manual repositioning occurs.

The processor can control the positioning indicator system to direct both rotation and translation of the base 108 during the manual repositioning. As shown in FIG. 6K, the processor can control the positioning indicator system to indicate a repositioning direction 606 in which the operator 112 translates the base 108 in the repositioning direction 606. As shown in FIGS. 6L and 6M, the processor can also control the positioning indicator system to indicate a repositioning direction 606 in which the operator 112 rotates the base 108 in the repositioning direction 606.

In FIG. 6N, the operator 112 has successfully manually repositioned the base 108 such that the base 108 is within the optimal base location envelope 110. In some implementations, at operation 600N, the processor controls the surgical manipulator assembly 104 to provide a success indicator 608. The success indicator 608 indicates that the manual repositioning of the base 108 is complete. In some implementations, the success indicator 608 is a specific sequence or pattern provided by the positioning indicator system. In some implementations, the success indicator 608 includes an audio confirmation, a tactile confirmation, or other signal to indicate success to the operator. In some examples, the positioning indicator system also provides indications to the operator when the base 108 is outside of the optimal base location envelope 110.

After the repositioning of the base 108 has been successfully completed, the surgical operation can commence. The surgical tool can be inserted into the access port on the patient 102. A surgeon can remotely control the remotely controllable arm 106 of the surgical manipulator assembly 104 to control the surgical tool to perform the surgery.

In some implementations, performing a second manual repositioning may be beneficial to reposition the base 108 in a more optimal position. The operator 112 may issue a request to the processor to direct a second manual repositioning. In some examples, the processor detects that a second manual repositioning is beneficial and then alerts the operator 112 to perform the second manual repositioning. For example, an obstacle can be placed adjacent the surgical manipulator assembly 104 during the procedure after the initial manual repositioning is complete. The initial manual repositioning performed by the operator 112 may not be sufficient to avoid the obstacle. As shown in FIG. 6O, the optimal base location envelope is an initial optimal base location envelope 110 that does not account for an obstacle 612, e.g., an accessory cart, the patient, and/or an operator. In FIG. 6O, the obstacle 612 is sufficiently far from the surgical manipulator assembly 104 such that collision between the remotely controllable arm 106 and the obstacle 612 is unlikely. However, as shown in FIG. 6P, the obstacle 612 is moved to a position adjacent the surgical manipulator assembly 104, thus increasing the likelihood of collision.

In some implementations, the second manual repositioning may occur because the surgical tool 134 has to be moved to a new port location on the patient during the surgical procedure. The initial port position may require a base location that differs from the base location required for the new port position. In this regard, the new port position can result in a new reference point 162, in turn resulting in a new optimal base location envelope for the second manual repositioning. As a result, the processor directs the second manual repositioning such that the operator is guided to move the base 108 toward the new optimal base location envelope.

In some implementations, the processor directs a second manual repositioning. The processor initiates the second manual repositioning process, for example, when the arm or the surgical tool has been moved to the edge of a workspace boundary and the operator wishes to move the arm or the surgical tool beyond the workspace boundary. In such a case, the processor can trigger the second manual repositioning that accounts for a new workspace boundary, for example, that the operator defines using the manual demonstration process described herein. In some cases, the processor initiates the second manual repositioning process due to movement of an obstacle, e.g., movement of an operator or a device in the surgical environment 10.

As described with respect to FIGS. 3 to 5, the surgical manipulator assembly 104 includes obstacle detection sensors that can be used to detect the obstacles near the remotely controllable arm 106 of the surgical manipulator assembly 104. Upon detecting the obstacle 612, the processor can determine that the likelihood of collision is sufficiently large that the remotely controllable arm 106 should be repositioned away from the obstacle 612. While it may be possible that the joints can be actuated without movement of the base 108 to avoid collision between the remotely controllable arm 106 and the obstacle 612, in some examples, it may be beneficial to direct a second manual repositioning of the base 108 to achieve other goals, as described with respect to FIGS. 4 and 5. For example, the second manual repositioning may beneficially improve the range of motion index of the joints of the remotely controllable arm 106 in light of the new obstacle 612 that may impede the range of motion of some of the joints. As shown in FIG. 6P, the processor can compute a new optimal base location envelope 110 that accounts for the new obstacle. The processor controls the positioning indicator system to indicate a repositioning direction 606 for the second manual repositioning. The operator 112 can then perform the second manual repositioning in accordance to the repositioning direction 606 such that the base 108 and the remotely controllable arm 106 are moved away from the obstacle 612, thereby reducing the risk of collision with the obstacle 612.

Additional Implementation Alternatives

The systems described above may optionally include one or more of the following features in addition to, or in place of, the features discussed above.

While the arm 106 is described as being remotely controllable, in some implementations, the arm 106 is controlled by an operator at a location within the same room as the arm 106. For example, if the arm 106 is used during a medical procedure, the operator can control the arm 106 from a bedside of the patient.

While described as including the cart 11, in some cases, the setup assembly 109 corresponds to a platform attached to a gantry above the floor surface 20 and mounted onto walls or ceilings of the surgical environment 10. The operator 112 can move the platform along the gantry to perform the manual repositioning. The gantry can include a braking mechanism coupled to, for example, rails attaching the base 108 to the gantry. The positioning indicator system can include the braking mechanism associated with the rails.

The surgical system 100 represents an example of a surgical system that can include methods, systems, and devices that can guide manual repositioning. The surgical system 100 and the methods described herein can be modified to include alternative or additional features. Some features of the surgical system 100 may also be omitted. In some cases, these modifications can additionally change the operation of the surgical system 100, e.g., the operations 402, 404, 406-408, 410, 412, 414, and 416 and the operations 600A to 600P.

In some implementations, the setup joints and the joints of the remotely controllable arm 106 and/or the setup assembly 109 can include a combination of revolute and prismatic joints different from the combination described with respect to FIG. 2A. Each of the joints can provide translational degrees of freedom, rotational degrees of freedom, or combinations thereof. A joint may include multiple rotational degrees of freedom, e.g., rotation about multiple independent axes. A joint may include multiple translational degrees of freedom, e.g., translation along multiple independent axes. For example, while the setup joints 142b-142c and

148*a*-148*g* have been described as revolute joints, in some examples, one or more of these joints 142*b*-142*c*, 148*a*-148*g* can allow for translational degrees of freedom, thus enabling relative translation between links of the setup arm 128 and the remotely controllable arm 106. The joint 142*a*, while described as a prismatic joint, can be a revolute joint that permits the remotely controllable arm 106 to pivot relative to the base 108. In some cases, a joint may allow for both relative rotation and translation between links. The remotely controllable arm 106 can include fewer or additional links and joints depending on the degrees of freedom desired for the given application.

The type of joints for the remotely controllable arm 106 and the setup arm 128 can vary in different implementations. In some examples, the remotely controllable arm 106 includes only powered joints while the setup arm 128 includes only passive joints. In some implementations, the surgical manipulator assembly 104 does not include both the remotely controllable arm 106 and the setup arm 128. For example, the remotely controllable arm 106 can include a single powered joint that couples the remotely controllable arm 106 to the cart 111 or the setup assembly 109. The processor 302 can selectively activate the single powered joint to drive the powered joint during the manual repositioning. The movement of the powered joint can maintain the position and/or orientation of the distal portion (or an item supported by the remotely controllable arm 106 such as a cannula 150 or a surgical tool 134) during the manual repositioning. In some implementations, the remotely controllable arm 106 and the setup arm 128 together can include two or more powered joints. The processor 302 can selectively activate each of the powered joints to maintain the position and/or orientation of the distal portion (or an item supported by the remotely controllable arm 106 such as a cannula 150 or a surgical tool 134) relative to a reference, such as relative to the reference point 162, during the manual repositioning.

In some cases, the remotely controllable arm 106 and the setup arm 128 include a selectively releasable passive joint. The selectively releasable passive joint can include, for example, a braking mechanism that maintains the position of the passive joint. In this regard, the remotely controllable arm 106 can include a powered joint and the selectively releasable passive joint. During the manual repositioning of the base 108, the processor 302 can selectively activate the powered joint and selectively release the passive joint to use reactive forces to move the passive joint while maintaining the position and/or orientation of the distal portion (or an item supported by the remotely controllable arm 106 such as a cannula 150 or a surgical tool 134).

While the surgical system 100 depicted in FIG. 1 shows a single surgical manipulator assembly 104, in some examples, the surgical manipulator assembly 104 may be one of multiple surgical manipulator assemblies, each of which includes a remotely controllable arm. Each of the remotely controllable arms can include a surgical tool, and manually repositioning of the bases of each of the surgical manipulator assemblies can be directed using the methods described herein. Furthermore, each of the remotely controllable arms can include a corresponding reference point that serves a remote center of motion. The manual repositioning of each of the bases can occur while powered joints for the surgical manipulator assemblies are actuated to maintain the positions of the respective distal portions of the surgical manipulator assemblies (or items supported by the surgical manipulator assemblies such as cannulas, surgical tools, other instrumentations or accessories, etc.). In some cases, the processor can detect other surgical manipulator assemblies using the obstacle detection sensors and consider the other surgical manipulator assemblies to be obstacles within the surgical environment. In this regard, the obstacle data used by the processor to direct the manual repositioning of the base can include the position of the other surgical manipulator assemblies. In some implementations, during a manual repositioning of a base for a first arm, a powered joint of a second arm is driven to avoid collision between the first arm and the second arm when the first arm is being manually repositioned.

In some examples, rather than being a surgical manipulator assembly 104 having a single arm 106, the surgical manipulator assembly includes multiple arms each having a surgical tool. Each of the surgical tools can be inserted into separate access ports. During the manual repositioning of the base 108, the processor can control joints of each of the multiple arms to maintain the position and/or orientation of the distal portion of each arm (or an item supported by each arm, such as a cannula or a surgical tool) relative to its respective access port. Each of the arms extend from a single base 108. To direct the manual repositioning, the processor can consider optimal positions for each of the arms and direct the manual repositioning of the base to improve optimality for each of the arms. In some implementations, it may not be possible to maximize the optimality score for the positions and orientations for each of the arms. In such cases, the optimization strategies can include a net optimality score that accounts for optimality scores for each of the arms. As part of the optimality strategies, the optimality score for a particular arm can be weighed more heavily than other arms. In this regard, optimizing the net optimization score results in a position and orientation for the particular arm that is closer to the optimal position and orientation for the particular arm given the data related to the surgical procedure to be performed.

While the positioning indicator system 304 has been described as having indicator lights 200 on the column 138, in some implementations, the configuration of the positioning indicator system can differ in position, mechanism, and in other respects. For example, in some implementations, the positioning indicator system 304 includes a mechanical dial, instead of lights, that visually indicates the direction that the base 108 of the surgical manipulator assembly 104 should repositioned.

Figure 7:
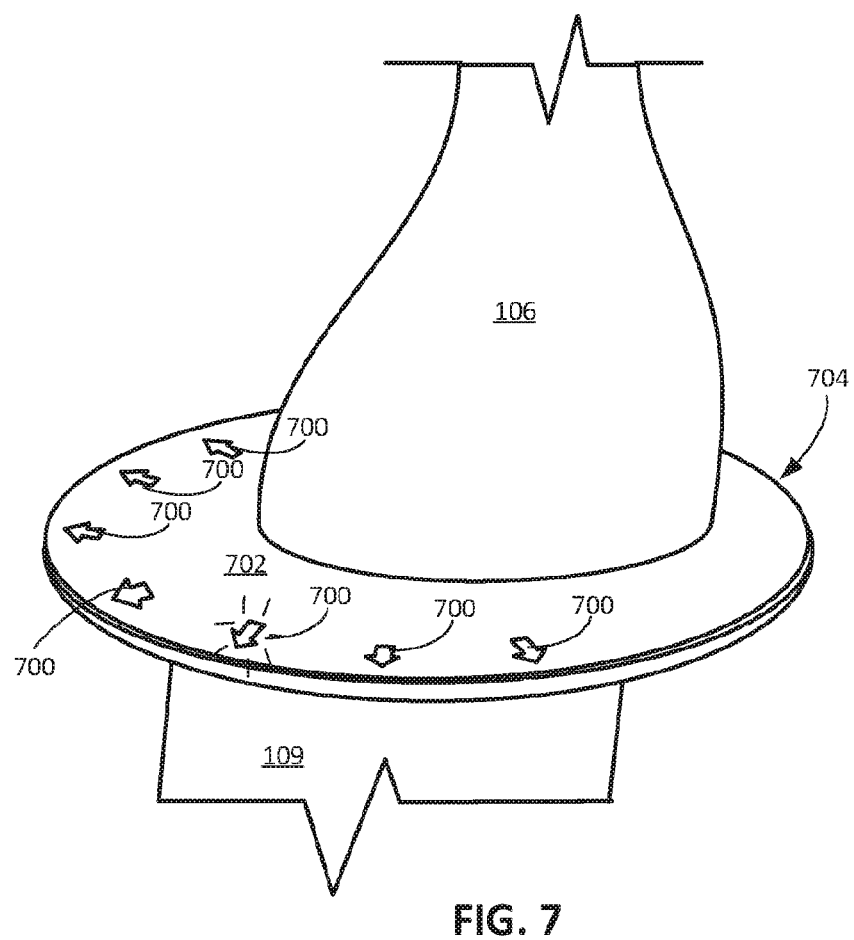
FIG. 7 is a perspective view of an example of a base of a manipulator assembly with indicator lights.

While the indicator lights 200 can project the light on the floor surface of the surgical environment, in some examples, the indicator lights can project light onto a portion of the base 108. In some cases, the indicator lights can be positioned on a portion of the base and can be directly illuminated to indicate a direction for the manual repositioning. For example, as shown in FIG. 7, indicator lights 700 can be positioned along a proximal portion 702 of a base 704.

The positioning indicator system 304, though described as part of the surgical manipulator assembly 104, may in some examples be a system independent from the surgical manipulator assembly 104. The positioning indicator system can be a visual or audio indicator system separate from the surgical manipulator assembly 104. The positioning indicator system may be part of an audio system configured to emit audible signals that can be heard within the surgical environment. The audible signals can indicate the direction to move the base. In some examples, the positioning indicator system is a visual indicator system, e.g., a ceiling-mounted projector, floor lights, and the like, that illuminate the floor surface to indicate the direction that the base should be moved.

While the positioning indicator system 304 has been described as providing indications of a desired repositioning direction toward which the base 108 should be moved to reach an optimal base position and/or orientation, in some implementations, the positioning indicator system 304 is operated in a different manner to guide the manual repositioning of the base 108. For example, the positioning indicator system 304 can provide an indication of an estimated distance between an optimal location of the base 108 and a current location of the base 108. If the positioning indicator system 304 includes an indicator light (e.g., one of the indicator lights 200), an intensity, a wavelength, or a color of illumination emitted by the indicator light can vary as the estimated distance varies. If the positioning indicator system 304 includes a speaker or other audible indication device, an intensity, a pitch, a frequency, a volume, or a verbal instruction of the audible indication provided by the speaker can vary as the estimated distance varies. For example, the intensity, the pitch, the frequency, or the volume of the audible indication can increase as the estimated distance decreases, and the intensity, the pitch, the frequency, or the volume can decrease as the estimated distance increases. Alternatively, a verbal instruction of the audible indication verbally expresses that the base 108 is being moved away from the optimal base location as the estimated distance increases or that the base 108 is being moved closer to the optimal base location as the estimated distance decreases.

In some implementations, rather than providing an indication of a single parameter such as a repositioning direction, the positioning indicator system 304 provides indications of multiple parameters related to a location of the base 108 during the manual repositioning. For example, the indications can be indicative of one or more parameters including one or more of: a repositioning direction for the base 108, a relative distance between a current location of the base 108 and an optimal location of the base 108, a relative angle between a current orientation of the base 108 and an optimal angle of the base 108, a relative distance between the base 108 and an expected location of an obstacle, a relative distance between the base 108 and a limit of a range of motion of the base 108, successful repositioning of the base 108 to a location within the optimal base location envelope, or that the base 108 is at a location outside of the optimal base location envelope. In some cases, a single indicator device of the positioning indicator system 304 is operable to provide indications of multiple parameters. For example, a single indicator light (e.g., one of the indicator lights 200) can be operable to provide an indication of a relative distance between the base 108 and the optimal location of the base 108 as well an indication of the repositioning direction for the base 108. Illumination of the indicator light can be indicative of the repositioning direction for the base 108, and an intensity of the illumination of the indicator light can be indicative of the relative distance between the current location of the base 108 and the optimal location of the base 108.

Each indication provided by the positioning indicator system 304 can be provided through one or more modalities. For example, when a single indication is provided, the indication can be provided through multiple modalities, e.g., through two or more of an audible indication, a visual indication, or a tactile indication. When multiple indications indicative of different parameters are provided, each of the indications can be provided through the same modality or through different modalities. For example, one indication can be provided by a visual indicator device, and another indication can be provided by an audible indicator device. Alternatively, multiple indications can be provided by a visual indicator device, and another indication can be provided by a tactile indicator device.

In some examples, the positioning indicator system includes a display that graphically depicts the current location of the base 108 and preferred locations or locations of the base 108. The graphic display can depict these locations in a plan view, and can depict other obstacles within the surgical environment 10 to give the operator context when manually repositioning the base 108. The operator successfully moves the base 108 to the optimal base location envelope 110 when the visual indicator of the current location of the base 108 matches the visual indicator of one or more of the preferred locations of the base 108.

In some examples, the positioning indicator system can illuminate an area of the floor surface corresponding to the optimal base location envelope to indicate the direction that the base should be moved. The positioning indicator system can also project a desired location onto the floor surface, so that the user manually pushes the base toward the desired location. If the projector is attached to the remotely controllable arm 106 or the base 108, the position of the projector can be updated as the remotely controllable arm 106 or the base 108 move during the manual repositioning. In this regard, the projection of the desired location remains at the desired location even as the remotely controllable arm 106 and the base 108 are repositioned.

The positioning indicator system 304 can alternatively or additionally include tactile indications of the repositioning direction. For example, if the cart 111 includes the wheels 136 and the wheels 136 include the braking mechanism, the processor 302 can control the braking mechanism as part of the positioning indicator system 304. The processor 302 can activate the braking mechanism if the operator 112 attempts to move the base 108 in a direction away from the optimal base location envelope 110 and can deactivate the braking mechanism if the operator 112 moves the base 108 in a direction toward the optimal base location envelope 110. The resistance provided by the activation of the braking mechanism can therefore provide a tactile indication for the operator 112, thereby guiding the manual repositioning of the base 108.

As described herein, the joints can be actuated so that the joints are positioned near centers of their ranges of motion. In examples in which the processor 302 cannot control the joints to be actuated such that each of the joints are near the centers of their ranges of motion during the manual repositioning, the positioning indicator system can provide some indication that one or more the joints are near a periphery of their ranges of the motion. For example, the processor 302 may be unable to reposition a joint away from the periphery of its range of motion without overriding the goal of maintaining the position and/or orientation of the distal portions of arm (or an item supported by the arm such as a cannula or a surgical tool 134). To inhibit movement of the joint beyond the range of joint states, the processor 302 can activate the positioning indicator system 304 to indicate that the base 108 should not be moved in a direction, as movement of the base 108 in that direction would cause the joint to move beyond the range of available joint states for the joint. In some examples, the processor 302 can activate the braking mechanism of the base 108 to prevent further movement of the base 108 that could cause the joint to move beyond the range of joints states.

In some implementations, the positioning indicator system controls the powered joints of the remotely controllable arm 106 such that they are only movable in a direction that would cause the base 108 to move toward the optimal base location envelope 110. The operator 112 would then push the base 108 or the joints such that the base 108 is moved toward the optimal base location envelope 110. The resistance to movement of the powered joints in directions that would cause the base 108 to move in a direction away from the optimal base location envelope 110 serves as a tactile indication to guide the operator 112 to manually reposition the base toward the optimal base location envelope 110.

As described herein, the processor 302 can use the indices to generate signals to actuate the joints while the manual repositioning of the base 108 occurs. In some implementations, in addition to controlling the joints to maintain the position and/or orientation of the distal portion of arm (or an item supported by the arm such as a cannula or a surgical tool 134), the processor 302 may control the joints based on the indices. For example, specific configurations of the joints of the remotely controllable arm 106 can be challenging during the surgery. Upon determining that the joints are in one of these challenging configurations, the processor 302 may actuate the joints to avoid this configuration while maintaining the position and/or orientation of the distal portion of arm (or an item supported by the arm such as a cannula or a surgical tool 134). For example, a revolute joint of the remotely controllable arm 106 may be driven from a downward oriented apex configuration to an upward oriented apex configuration to inhibit collisions with an adjacent arm, equipment, or personnel; to enhance a range of motion of the distal portion of the remotely controllable arm 106 (or an item supported by the remotely controllable arm 106 such as a cannula or a surgical tool 134); in response to physiological movement of the patient 102 such as patient breathing or the like; in response to repositioning of the patient 102, such as by reorienting a surgical table; and the like.

In some examples, the manual repositioning of the base 108 occurs before the surgery is performed. However, the manual repositioning of the base 108 may also occur during the surgery. The operator 112 may also manually reposition the base 108 multiple times during a procedure.

While FIGS. 6O and 6P show that a second manual repositioning can occur due to a new obstacle 612 entering the vicinity of the base 108 of the surgical manipulator assembly 104, in some implementations, other or additional parameters can change that can result in the processor 302 determining that a second manual repositioning may be beneficial. In some implementations, different surgical tools can result in different workspace requirements. As a result, if a surgical tool is "switched" with another surgical tool (e.g., the surgical tool dismounted from the arm and a different surgical tool mounted onto the arm) during the surgery, the processor 302 can detect that the surgical tool has been switched and compute a new optimal base location envelope. If the base is not within the new optimal base location envelope for the currently mounted, different surgical tool, after the surgical tool has been switched, the processor 302 can direct a second manual repositioning in light of the different surgical tool.

In some cases, the remotely controllable arm 106 may be subject to an external force during the surgery that causes the base 108 to shift from its position. The pose sensors 308 can detect articulation about the joints 142a-142c and 148a-148g due to the external force or can detect movement of the base 108 due to the external force. Due to the movement of the components of the surgical manipulator assembly 104, the processor 302 may determine that the base 108 may need to undergo a second manual repositioning so that the base 108 can be repositioned within the optimal base location envelope 110.

In some examples, the surgical tool 134 may be moved from one access port to another access port during the surgery. When the surgical tool 134 is moved to the new access port, the processor 302 can direct a second manual repositioning of the base 108. Because the new access port may be positioned in a different area on the patient 102, the extent of the workspace necessary for the surgical tool 134 to perform the surgical procedure may change as well. Thus, after placement of the surgical tool 134 in the new access port, the operator 112 may demonstrate a new extent of the workspace. With these changes in both the position of the access port (e.g., the port data 514) and the extent of the workspace (e.g., the procedure data 504), the processor 302 may compute new values for the indices of the current pose of the remotely controllable arm 106 and direct the second manual repositioning in light of these new index values.

While demonstration of the workspace has been described herein as including a physical movement of the surgical tool 134 through the workspace, in some examples, the operator 112 can demonstrate the workspace without physically moving the surgical tool 134. For example, the operator 112 may graphically indicate on a display the extent of the workspace. The operator can specify the extent of the workspace using a computing device with a touchscreen display. By operating the touchscreen display, the operator can delineate the extent of the workspace. The computing device can deliver an input indicative of the extent of the workspace to the processor 302. In some examples, the operator can use a physical tool that can be detected by a sensor on the surgical manipulator assembly 104. The physical tool can be a hand or a pointing device that can demarcate the workspace. The sensor can, for example, optically detect the position of the physical tool and then generate signals for the processor 302, which in-turn determines extent of the workspace based on the sensor signals.

While the processor 302 has been described to guide the manual repositioning of the base 108, in some examples, the processor 302 may guide the manual repositioning of other parts of the surgical system 100. In some examples, the processor 302 can guide the manual repositioning of the cart 111 toward an optimal cart location envelope. Other parts of the surgical system 100 may add additional degrees of freedom that can be used to optimize a greater number of goals or indices. For example, if the operating table 123 is movable across the floor surface 20, the positioning indicator system 304 may include positioning indicators that signify a direction that the operating table 123 should be moved to achieve the goal or goals of the optimization strategies. The positioning indicator system 304 can include positioning indicators for the base 108 of the surgical manipulator assembly 104 as well as positioning indicators for the operating table 123. The base 108 may include a braking mechanism that is activated when the operating table 123 is being manually repositioned. The operating table 123 may also include a braking mechanism that is activated when the base 108 is being manually repositioned. In addition, during the manual repositioning of the operating table 123, at least one of the powered joints of the remotely controllable arm 106 can be actuated to maintain the position and/or orientation of the distal portion of arm (or an item supported by the arm such as a cannula or a surgical tool 134). The position and/or orientation may be maintained relative to an appropriate reference, such as the reference point 162.

In some examples, if the remotely controllable arm 106 includes passive joints, each of the passive joints can include positioning indicators. The processor 302 can control the positioning indicators of each of the passive joints to control the manual repositioning of each of the passive joints. During the manual repositioning of a passive joint, a braking mechanism can prevent movement of the base 108. Each of the other passive joints, if present, can also include a braking mechanism so that the other passive joints do not move during the manual repositioning of the passive joint. The processor can control active joints of the remotely controllable arm 106 to maintain the position and/or orientation of the distal portion of arm (or an item supported by the arm such as a cannula or a surgical tool 134) relative to a reference, such as relative to the reference point 162, during the manual repositioning of the passive joint.

While the remotely controllable arm 106 is described as being mounted to the cart 111, in some implementations, the remotely controllable arm may be attached to a stationary or movable table. Referring to example depicted in FIG. 8A, a wheeled robotic table system 800A includes a table base 802A. A remotely controllable arm 804A includes an arm base 806A movably attached to the table base 802A. For example, the arm base 806A is attached to the table base 802A at a prismatic joint 808A that allows the arm base 806A to translate along the table base 802A. In some implementations, the arm base 806A is attached to the table base 802A at a rotational joint that allows the arm base 806A to rotate about the table base 802A. In other examples, various remotely controllable arms (e.g. arm 804A) are designed to be attached to different portions of a table system (e.g. table system 800A). Example attachment portions include a base of the table system, a surface of the table system, one or more rails proximate to the table surface (if such rails exist), etc. In some implementations, the arm base 806A is removably attached to the table base 802A, and may be removed when not to be used in the operation. In some implementations, the arm 804A is folded under the table surface when not to be used in the operation.

Figure 8A:
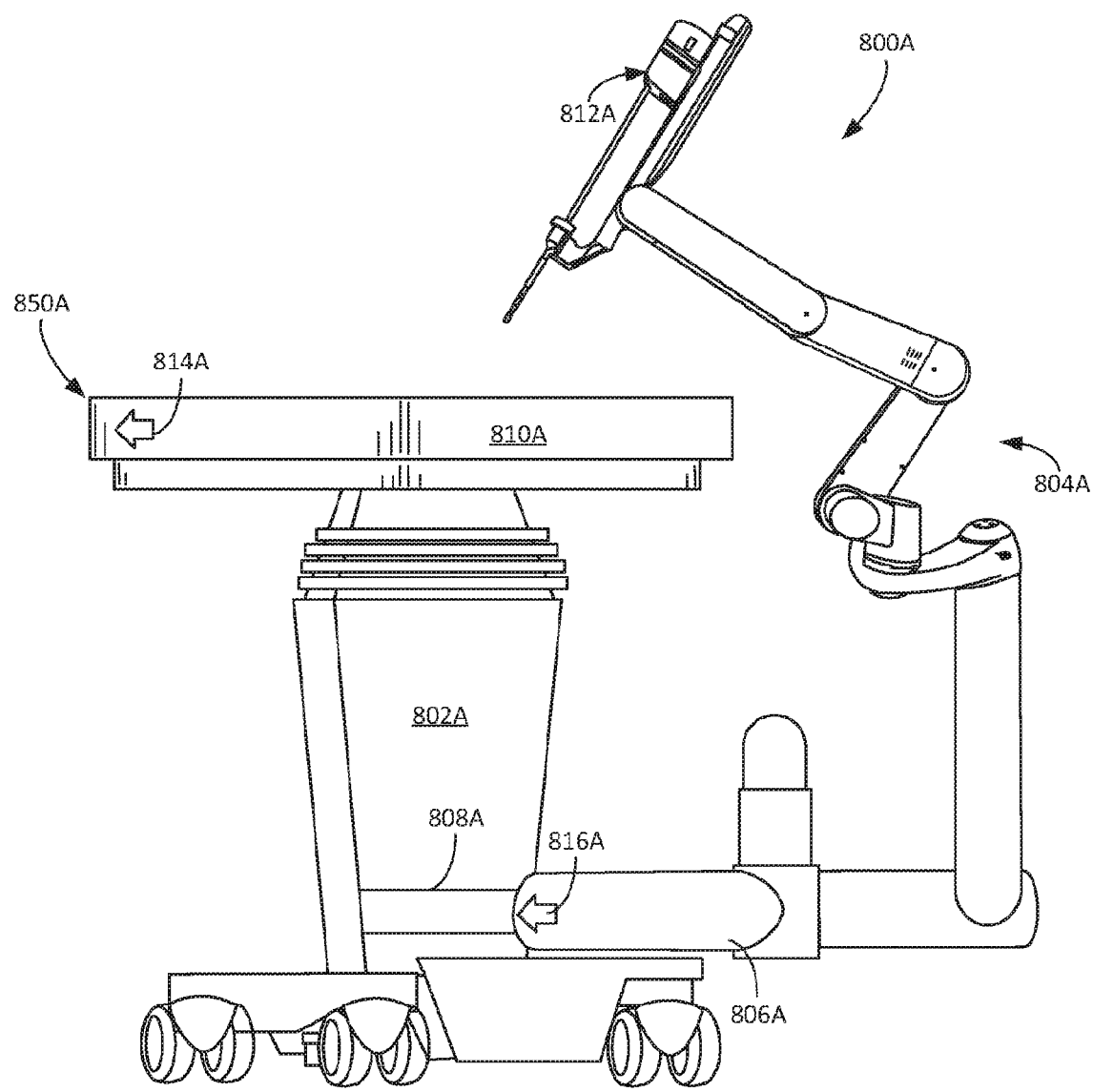
FIG. 8A is a perspective view of an example robotic table system.

In the FIG. 8A example, a table surface 810A is positioned on the table base 802A and is movable relative to the table base 802A. For example, the table surface 810A may be pivoted about the table base 802A or rotated about the table base 802A. In other examples, the table surface 810A may be stationary relative to the table base 802A.

Before a surgery is performed, an operator may manually reposition the table surface 810A relative to the table base 802A. The operator may also manually reposition the arm base 806A relative to the table base 802A. In this regard, a processor can direct a first manual repositioning using a first indicator 814A for the table surface 810A and a second manual repositioning using a second indicator 816A for the arm base 806A. The processor can determine a combination of an optimum table surface location and an optimum arm base location based on the indices described herein. During each of the two instances of manual repositioning, the processor can control joints of the arm 804A such that the position and/or orientation of a distal portion of arm 804A (or an item supported by the arm such as a cannula or a surgical tool 812A) is maintained relative to a reference (e.g. a reference frame, one or more reference directions, a reference point, etc.), as described in greater detail herein.

The table system 800A shown in FIG. 8A includes a plurality of wheels that allow the table system 800A to be repositioned with respect to a separately movable surgical manipulator assembly (e.g., surgical manipulator assembly 104), or to be moved around the operating area or from room to room, etc.

Figure 8B:
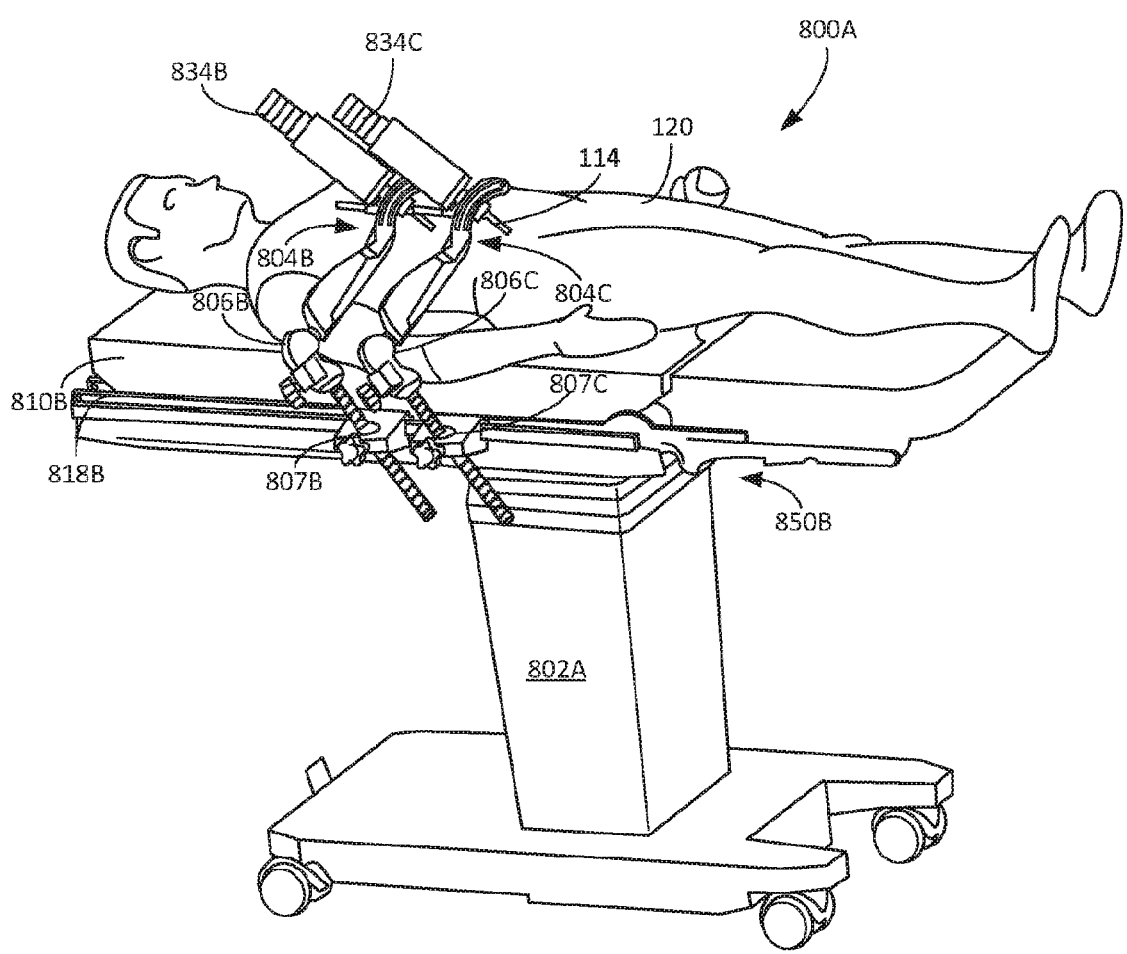
FIG. 8B is a perspective view of another example controllable arm.

FIG. 8B is a perspective view of another example controllable arm that may be attached to a stationary or movable table. A wheeled table 850B includes a table base 802B. A table surface 810B is positioned on the table base 802B. The table surface 810B can be used to support a work piece such as patient 820B, cadaver, body part, or a non-human work piece. In the example shown in FIG. 8B, two remotely controllable arms 804B, 80C includes arm bases 806B, 806C that may be removably attached to a number of different locations along a table rail 818B.

During operation, the controllable arms 804B, 804C are driven to move tools 834B, 834C within associated workspaces. In some implementations, the controllable arms 804B, 804C are teleoperable and include remotely operable powered joints that, when driven, reposition and reorient the tools 834B, 834C with respect to the workspace. In some implementations, and like the other remotely controllable arms described herein, the controllable arms 804B, 804C can also be operated directly through input applied directly on the links or joints of the controllable arms 804B,C, allowing direct operator manipulation of the controllable arms 804B, 804C.

Figure 8C:
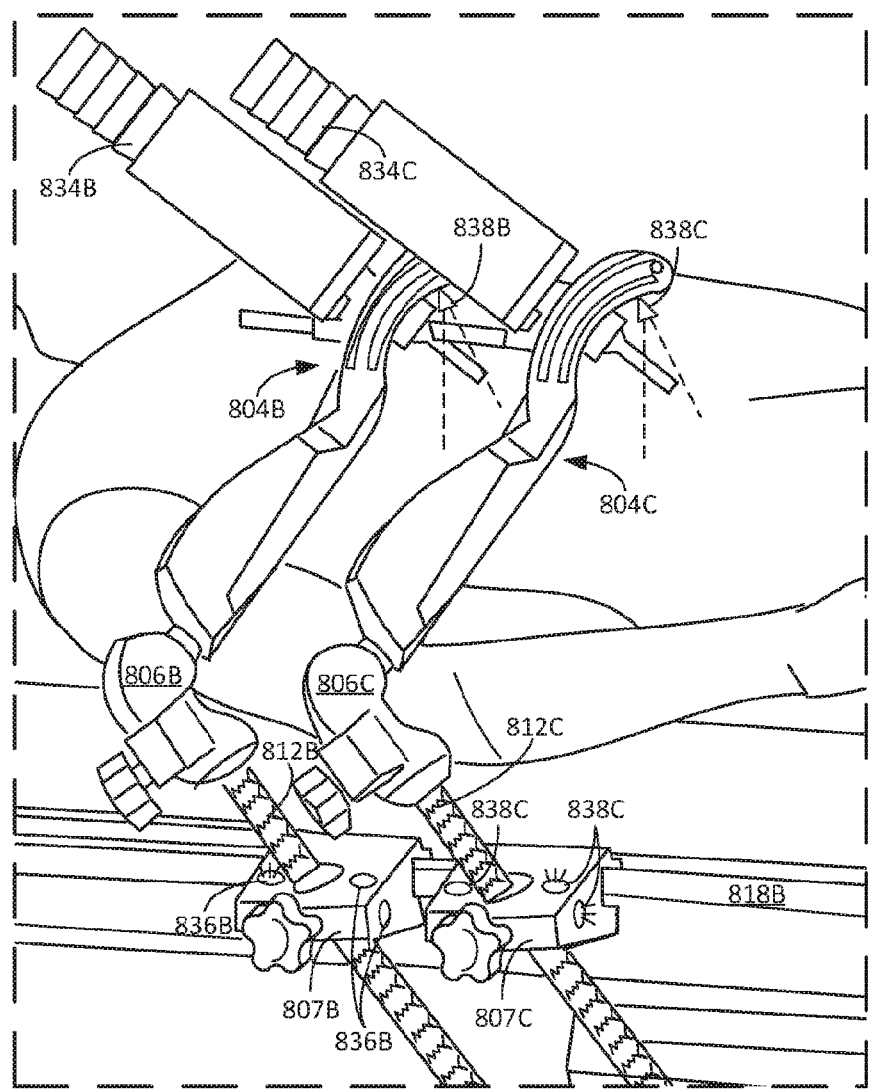
FIG. 8C is a perspective view of an indicator system for the controllable arm of FIG. 8B.

Similar to what has been described for the robotic table system 800A, before a surgery is performed, an operator may manually reposition the table surface 810B relative to the table base 802B. The operator may also manually reposition the arm bases 806B, 806C relative to the table rail 818B, or move one or more of the arms 804B, 804C to one or more other table rails (not shown) on other side(s) of the table. In this regard, a processor can operate a positioning indicator system (e.g., similar to the positioning indicator system 304) to direct a manual repositioning using indicators for the arms 804B, 804C. For example, referring to FIG. 8C, the positioning indicator system can include first indicator lights 836B, 836C similar to the indicator lights 200 described herein. The first indicator lights 836B, 836C are positioned on or proximate passive joints 807B, 807C connecting the arm bases 806B, 806C to the table rail 818B. The first indicator lights 836B, 836C are operated to indicate directions that the passive joints 807B, 807C (and thereby the arm bases 806B, 806C) should be moved to optimize the positions of the arm bases 806B, 806C relative to the tools 834B, 834C. In some implementations, rather than including passive joint 807B, 807C separate from the arm bases 806B, 806C, the passive joints 807B, 807C correspond to the arm bases 806B, 806C.

During manual repositioning of the arm bases 806B, 806C, the arm bases 806B, 806C are jointly moved with the passive joints 807B, 807C and thus move along the table rail 818B. Because movement of each of the passive joints 807B, 807C is limited to movement along the table rail 818B, the direction indicated by the indicator lights 836B, 836C for each of the passive joints 807B, 807C can be selected from two directions: a direction toward one end of the table rail 818B or a direction toward the other end of the table rail 818B. In such cases, during the manual repositioning, the operator is guided to move the arm bases 806B, 806C and the passive joints 807B, 807C relative to the table surface 810B along the table rail 818B according to the indication provided by the first indicator lights 836B, 836C. As described herein, the positions and/or orientations of the tools 834B, 834C or the distal portions of the arms 804B, 804C are maintained during the manual repositioning. Alternatively or additionally, the positioning indicator system can include second indicator lights 838B, 838C that project lights toward the table surface 810B or toward the work piece (e.g., the patient 820B) to further indicate the directions in which the arm bases 806B, 806C should be moved.

In some implementations, the arm bases 806B, 806C are movable relative to the tools 834B, 834C in manners other than sliding along the table rail 818B. The manual repositioning of the passive joints 807B, 807C with the arm bases 806B, 806C corresponds to a first manual repositioning, and the arm bases 806B, 806C are further repositioned relative to the passive joints 807B, 807C in a second manual repositioning. For example, links 812B, 812C coupled to the arm bases 806B, 806C can be movable relative to the passive joints 807B, 807C in insertion motions or roll motions, thereby causing relative translation or reorientation of the arm bases 806B, 806C and the tools 834B, 834C. The first indicator lights 836B, 836C or the second indicator lights 838B, 838C can be operated to provide the indication to guide the second manual repositioning of the arm bases 806B, 806C (and hence the links 812B, 812C). As described herein, the positions and/or orientations of the tools 834B, 834C or the distal portions of the arms 804B, 804C are maintained during the second manual repositioning.

The obstacle data 510 is described as being indicative of locations of obstacles in the workspace. While obstacles are described as including equipment in the workspace, other obstacles are possible. In some implementations, the obstacle data 510 include data indicative of obstacles include expected locations of any operators in the surgical environment 10, uneven floor surfaces, or other obstacles in the workspace that may impede movement of the base 108 or the remotely controllable arm 106. In some implementations, referring back to FIG. 8B, the obstacle data 510 include data indicative of the locations of the ends of the table rail 818B relative to the locations of the arm bases 806B, 806C. The processor directs the manual repositioning based on locations of the ends of the table rail 818B to avoid directing the operator to move the arm bases 806B, 806C beyond their allowable ranges of motion along the table rail 818B. Because the passive joints 807B, 807C are configured to be locked to the table rail 818B to support the arm bases 806B, 806C and hence the arms 804B, 804C above the table surface 810B, the ends of the table rail 818B limit the ranges of motion of the passive joints 807B, 807C and hence the arm bases 806B, 806C. The processor can direct the manual repositioning of the arm bases 806B, 806C such that the operator is not guided to move the passive joints 807B, 807C beyond their allowable range of motion.

Returning now to the example shown in FIG. 2 and associated figures, the wheels 136, in some implementations, are powered wheels that can be controlled by the processor 302 to move the base 108 about the floor surface 20. The wheels 136 may include a drive mechanism that allows the processor 302 to control the orientation of the wheels 136 to facilitate or inhibit repositioning. For example, the processor 302 can control the orientation of wheels 136 such that the wheels are aimed to roll along a repositioning direction or not to roll along a non-repositioning direction. Thus, the processor 302 can control the wheels so movement of the base 108 in directions that are not the repositioning direction is inhibited.

The wheels 136 may also include actuators such that, during the manual repositioning, the processor 302 can activate the actuators driving the powered wheels to assist the operator 112 in moving the base 108. In some implementations, the wheels 136 can include a steering system, such that the processor 302 can orient the wheels to preferentially move the cart 111 toward the optimal repositioning region when the operator pushes the base 108. Referring to FIG. 2, in some implementations, the surgical manipulator assembly 104 may include a handle 161 that the operator 112 can push and pull to move the base 108. The handle 161 may include a sensor that detects displacement of the handle 161. In response to the displacement of the handle 161 due to operator 112 pushing or pulling the handle 161, the processor 302 can activate the actuators driving the powered wheels to assist the operator during the manual repositioning of the base 108. The operator, for example, manipulates drive buttons, a joy stick, a dead man switch, or other appropriate user input devices to cause the powered wheels to move in a direction. In accordance to the processes described herein, the processor 302 can control the positioning indicator system to guide the operator 112 as the operator performs the manual repositioning using the input devices.

In some examples, the processor 302 can move the cart 111 within the surgical environment 10, and hence the base 108, by simply activating the actuators of the wheels 136 to drive the cart 111 toward the optimal base location envelope 110. The positioning indicator system can visually indicate the optimal base location envelope 110 to which the base 108 will be moved. An operator can provide confirmation to the processor that the visually indicated optimal base location envelope shown is appropriate. Alternatively or additionally, one or more joints of the surgical manipulator assembly 104 are powered, and the processor controls the wheels and/or the one or more joints to move the surgical manipulator assembly 104 and components of the surgical manipulator assembly 104 to optimal poses. In some cases, the processor activates the actuators of the wheels 136 and/or actuators of the one or more joints in response to the operator manually operating a switch. When the switch is deactivated, the processor stops operation of the actuators to stop further automated movement of the wheels and/or one or more joints.

In some implementations, the positioning indicator system may additionally indicate a path that the base 108 is to be moved. For example, if the base 108 is manually repositioned by the operator 112, the positioning indicator system can provide a visual indication of the path along the floor surface that the base 108 can be moved to enter the optimal base location envelope 110. In cases where the wheels are powered, the positioning indicator system can provide the visual indication of the optimal base location envelope 110 along with the path that the base 108 will move to reach the envelope. The operator 112 can then provide the confirmation of this visual indication to allow the processor to control the wheels to move along the path to the optimal base location envelope.

Figure 9A:
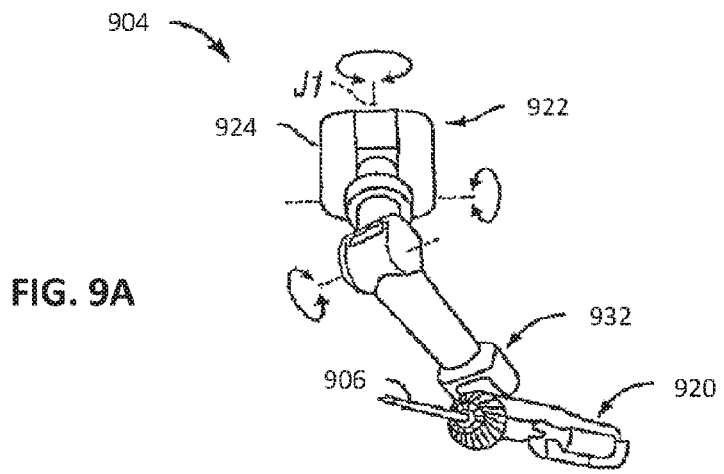
FIGS. 9A-9C are bottom, side, and back views of a controllable arm having a range of joint states for a given end effector position.
Figure 9B:
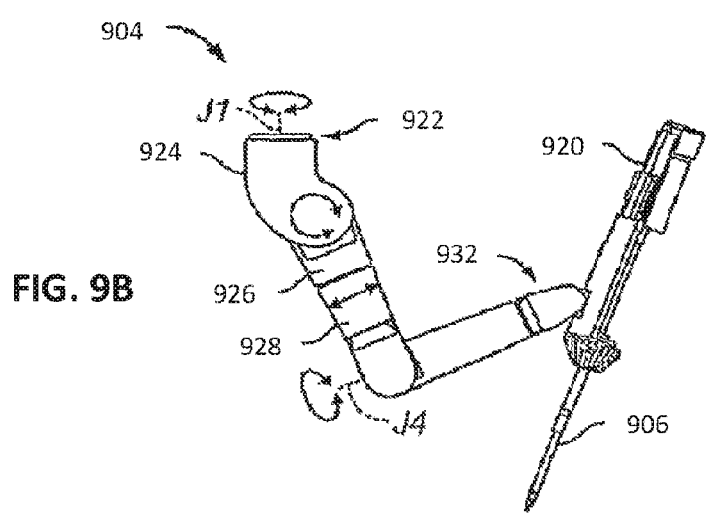
Figure 9C:
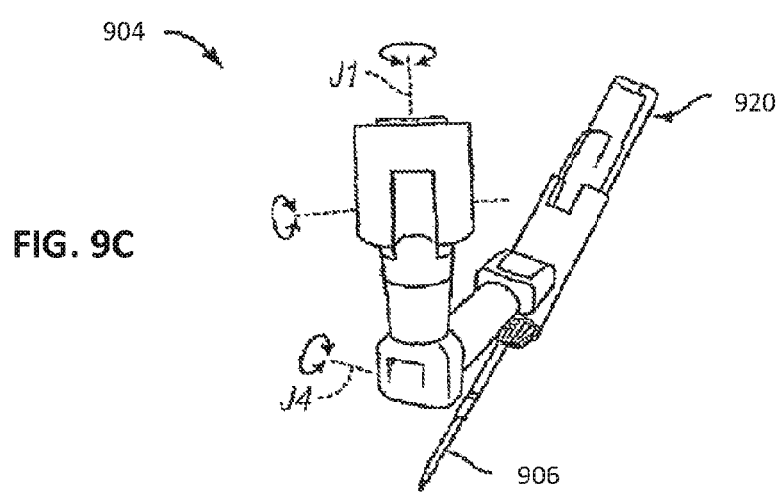

The remotely controllable arms 106 and 804A, B, C, as described herein, are examples of types of robotic manipulator arm assemblies envisioned within the scope of this disclosure. FIGS. 9A-9C depict bottom, side, and back views of another example robotic manipulator arm assembly 904 (also referred to as manipulator arm 904, or as remotely controllable arm 904 since it may be configured to be remotely controllable). In some implementations, the remotely controllable arm 904 is be coupled with a surgical tool 906 (also "surgical instrument 906") to affect movements of the instrument 906 relative to a base 902. As a number of different surgical instruments having differing end effectors may be sequentially mounted on each remotely controllable arm 904 during a surgical procedure (typically with the help of a surgical assistant), an instrument holder 920 will preferably allow rapid removal and replacement of the mounted surgical instrument 906.

The example remotely controllable arm 904 is mounted to the base 902 by a pivotal mounting joint 922 so as to allow the remainder of remotely controllable arm 904 to rotate about a first joint axis J1, with the first joint 922 providing rotation about a vertical axis in the exemplary implementation. Base 902 and first joint 922 generally include a proximal portion of remotely controllable arm 904, with the manipulator extending distally from the base toward instrument holder 920 and end effector 950.

Figure 9D:
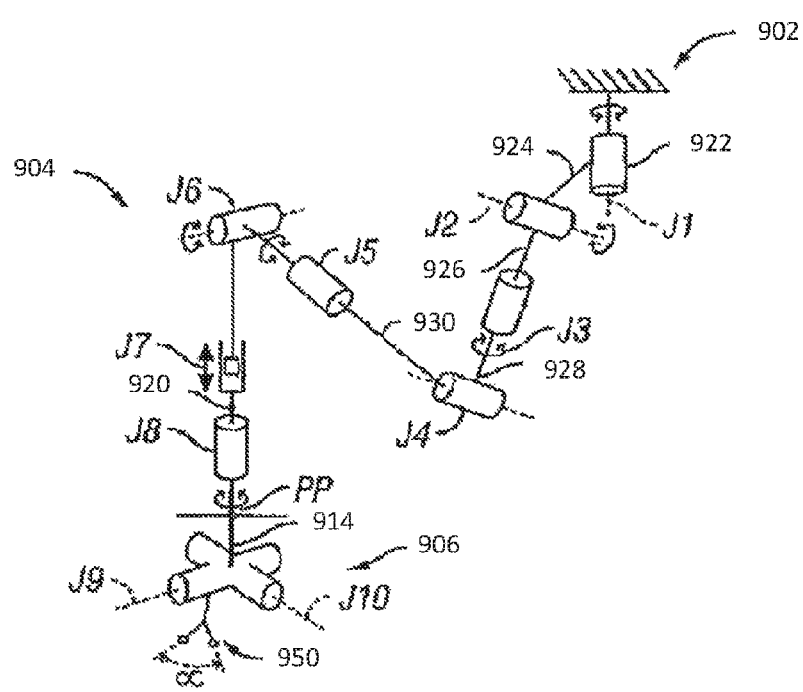
FIG. 9D is a schematic diagram illustrating the degrees of freedom of the controllable arm of FIGS. 9A-9C.

Describing the individual links of the controllable arm 904 as illustrated in FIGS. 9A-9C, along with the axes of rotation of the joints connecting the links as illustrated in FIG. 9D, a first link 924 extends distally from base 902 and rotates about first pivotal joint axis J1 at joint 922. Many of the remainder of the joints can be identified by their associated rotational axes in FIG. 9D. For example, a distal end of first link 924 is coupled to a proximal end of a second link 926 at a joint providing a horizontal pivotal axis J2. A proximal end of a third link 928 is coupled to the distal end of the second link 926 at a roll joint so that the third link generally rotates or rolls at joint J3 about an axis extending along (and ideally aligned with) axes of both the second and third links. Proceeding distally, after another pivotal joint J4, the distal end of a fourth link 930 is coupled to instrument holder 920 by a pair of pivotal joints J5, J6 that together define an instrument holder wrist 932. A translational or prismatic joint J7 of the remotely controllable arm 904 facilitates axial movement of instrument 906 and the elongate shaft 914 of the instrument 906 through the minimally invasive aperture, and also facilitates attachment of the instrument holder 920 to a cannula through which the instrument 906 is slidably inserted.

Distally of instrument holder 920, the surgical instrument 906 may include additional degrees of freedom. Actuation of the degrees of freedom of the surgical instrument 906 will often be driven by motors of the remotely controllable arm 904. Alternative implementations may separate the surgical instrument 906 from the supporting manipulator arm structure at a quickly detachable instrument holder/instrument interface so that one or more joints shown here as being on the surgical instrument 906 are instead on the interface, or vice versa. In other words, the interface between the surgical instrument 906 and remotely controllable arm 904 may be disposed more proximally or distally along the kinematic chain of the manipulator arm assembly 904 (which may include both the surgical instrument and the manipulator arm assembly 904). In the exemplary implementation, the surgical instrument 906 includes a rotational joint J8 proximally of the pivot point PP, which generally is disposed at the site of a minimally invasive aperture. A distal wrist of the surgical instrument 906 allows pivotal motion of end effector 950 about instrument wrist joint axes J9, J10. An angle α between end effector jaw elements may be controlled independently of the end effector 950 location and orientation. In some implementations, a positioning indicator system that emits a signal, e.g., an audible, a tactile, a visual, or other appropriate user-perceptible signal, guides manual repositioning of a joint of the remotely controllable arm 904 and/or the base 902. In some cases, the remotely controllable arm 904 includes multiple positioning indicator systems, each associated with a specific joint or the base 902 of the remotely controllable arm 904.

Figure 10:
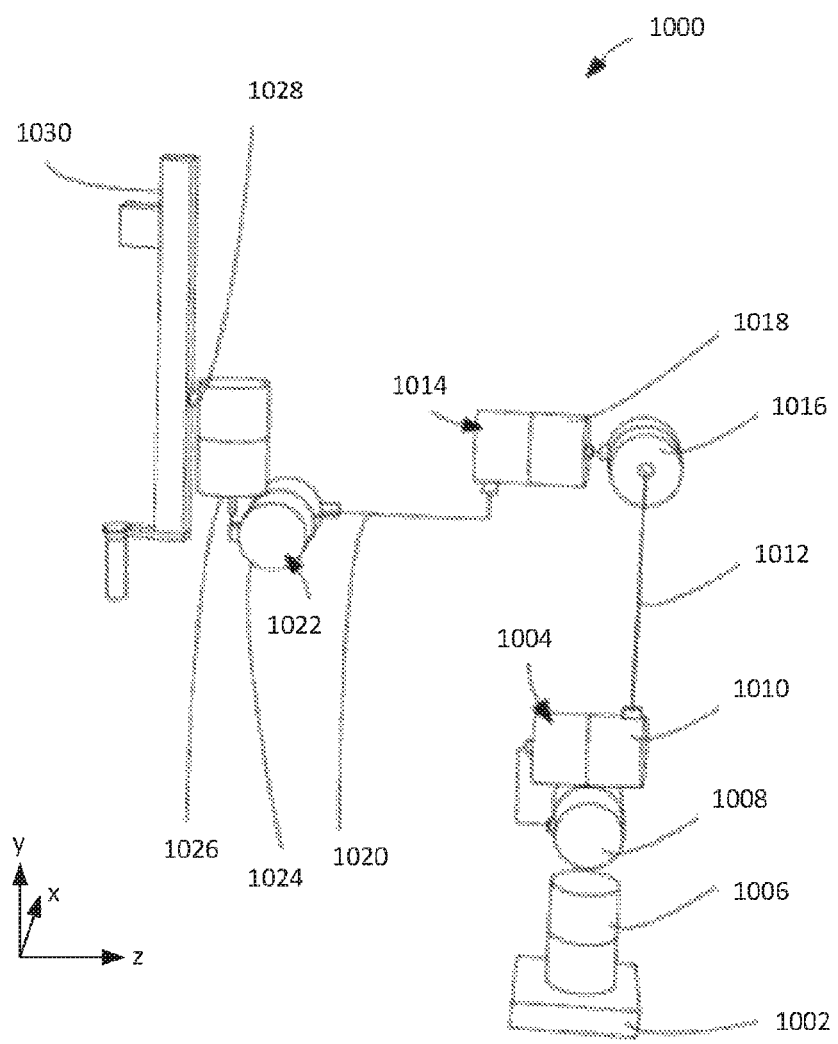
FIG. 10 is a schematic diagram illustrating degrees of freedom of another example of a controllable arm.

In another example, referring to FIG. 10, a controllable arm 1000 that may be made remotely controllable includes a base 1002 connected to a joint system 1004. A link 1012 connects the joint system 1004 to a joint system 1014, and a link 1020 connects the joint system 1014 to the joint system 1022. In some implementations, a joint 1006 rotates a portion of the remotely controllable arm 1000 that is distal to the base 1002 in a rotation relative to the base 1002, e.g., about the y-axis. In some implementations, a joint 1028 translates an instrument holder 1030 relative to joint system 1022, e.g., along the y-axis. Each joint and joint system is, for example, selectively operable to cause relative movement between portions of the remotely controllable arm 1000, e.g., translation and/or rotation between portions of the remotely controllable arm 1000.

The joint system 1004 is operable to cause relative rotation between the link 1012 and the joint system 1004. The joint system 1004 includes, for example, a first rotatable joint 1008 and a second rotatable joint 1010. The first joint 1008, when driven, causes relative rotation between the first joint 1008 and the second joint 1010, e.g., about the x-axis. The second joint 1010, when driven, causes relative rotation between the link 1012 and the second joint 1010, e.g., about the z-axis. The joint system 1014 is operable to cause relative rotation of the link 1020 and the joint system 1014. The joint system 1014, for example, includes a first joint 1016 and a second joint 1018. The first joint 1016, when driven, causes relative rotation between the first joint 1016 and the second joint 1018, e.g., about the x-axis. The second joint 1018, when driven, causes relative rotation between the second joint 1018 and the link 1020. The joint system 1022 is operable to cause relative rotation between the instrument holder 1030 and the joint system 1022. The joint system 1022 includes, for example, a first joint 1024 and a second joint 1026. The first joint 1024, when driven, causes relative rotation between the first joint 1024 and the second joint 1026, e.g., about the x-axis. The second joint 1026, when driven, causes relative rotation between the second joint 1026 and the instrument holder 1030, e.g., about the y-axis.

In some implementations, a positioning indicator system that emits a signal, e.g., an audible, a tactile, a visual, or other appropriate user-perceptible signal, guides manual repositioning of a joint, a joint system, and/or a base of the remotely controllable arm 1000. In some cases, the remotely controllable arm 1000 includes multiple positioning indicator systems, each associated with a specific joint, joint system, or base of the remotely controllable arm 1000.

The remotely controllable arms 106, 804A, 804B, 804C, 904, and 1000 are examples of remotely controllable arms. In some implementations, a remotely controllable arm includes a combination of joints in the examples of remotely controllable arms described herein. In this regard, in some implementations, a remotely controllable arm includes combinations of prismatic joints, rotational joints, and joint systems other than the combinations shown with respect to the remotely controllable arms 106, 804A, 804B, 804C, 904, and 1000.

The surgical systems (e.g., the surgical system 100) and robotic components of the surgical systems (e.g., the remotely controllable arm 106, the surgical manipulator assembly 104) described herein can be controlled, at least in part, using one or more computer program products, e.g., one or more computer programs tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment.

Operations associated with controlling the surgical systems described herein can be performed by one or more programmable processors executing one or more computer programs to perform the functions described herein. Control over all or part of the surgical systems described herein can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A robotic system comprising:
a base movable relative to a floor surface;
a remotely controllable arm extending from the base and configured to support a tool, the remotely controllable arm having a powered joint operable to move the tool when the tool is supported by the remotely controllable arm;
a positioning indicator; and
a processor communicatively coupled to the positioning indicator and the remotely controllable arm, the processor configured to:
operate the positioning indicator to direct a manual repositioning of the base relative to the floor surface; and
operate the powered joint to maintain a position of a distal portion of the remotely controllable arm during the manual repositioning.

2. The robotic system of claim 1, wherein the processor is further configured to:
operate the powered joint to maintain an orientation of the distal portion of the remotely controllable arm during the manual repositioning.

3. The robotic system of claim 1, wherein the processor is configured to operate the powered joint to maintain the position of the distal portion of the remotely controllable arm during the manual repositioning by:
operating the powered joint to maintain the position of the distal portion relative to a location of an access port on a patient through which the tool is to be inserted; or
operating the powered joint to maintain a position of a cannula held by the distal portion; or
operating the powered joint to maintain a position of the tool.

4. The robotic system of claim 1, further comprising:
a cart supported on the floor surface; and
a setup assembly comprising a passive joint, the setup assembly connecting the base to the cart,
wherein the processor is configured to operate the positioning indicator to direct the manual repositioning of the base relative to the floor surface by:
directing the manual repositioning while the cart is movable relative to the floor surface and the base is movable relative to the cart.

5. The robotic system of claim 1, further comprising a braking mechanism communicatively coupled to the processor, wherein the processor is further configured to operate the braking mechanism to inhibit movement of the base away from an optimal base location envelope.

6. The robotic system of claim 1, further comprising:
a setup assembly for attaching the base to a table, wherein the processor is configured to operate the positioning indicator to direct the manual repositioning of the base relative to the floor surface by:
directing the manual repositioning while the base is movable relative to the table.

7. The robotic system of claim 1, wherein:
the remotely controllable arm further comprises a second powered joint connected to the powered joint by one or more links,
the second powered joint is operable to move the tool when the tool is supported by the remotely controllable arm, and
the processor is configured to operate the powered joint to maintain the position of the distal portion of the remotely controllable arm during the manual repositioning by:
operating the powered joint and the second powered joint.

8. The robotic system of claim 1, further comprising a selectively releasable passive joint connected to the base by one or more links and supporting the base above the floor surface,
wherein the processor is configured to operate the powered joint to maintain the position of the distal portion of the remotely controllable arm during the manual repositioning by:
operating the powered joint and the selectively releasable passive joint to maintain the position of the tool.

9. The robotic system of claim 1, wherein the processor is configured to operate the positioning indicator to direct the manual repositioning of the base relative to the floor surface by:
directing the manual repositioning of the base based on a target range of joint states determined by the processor; or
directing the manual repositioning of the base based on an optimal base location envelope above the floor surface determined by the processor.

10. The robotic system of claim 1, wherein:
the positioning indicator comprises indicator lights selectively activatable by the processor, each of the indicator lights positioned to indicate a corresponding repositioning direction of the manual repositioning of the base; or the positioning indicator comprises a light projector, and the processor is configured to operate the positioning indicator to direct the manual repositioning of the base relative to the floor surface by: projecting light from the light projector toward the floor surface, the light indicative of a repositioning direction of the manual repositioning of the base.

11. The robotic system of claim 1, wherein:

the positioning indicator comprises an actuator or a braking mechanism, and the processor is configured to operate the positioning indicator to direct the manual repositioning of the base relative to the floor surface by:

controlling the positioning indicator to inhibit movement of the powered joint, or to provide a tactile indication to direct the manual repositioning of the base, during the manual repositioning of the base.

12. The robotic system of claim 1, wherein the processor is further configured to:

operate the positioning indicator to alert an operator during the manual repositioning of the base that the base is within an optimal base location envelope; or operate the positioning indicator to alert the operator during the manual repositioning of the base that the base is outside of the optimal base location envelope.

13. The robotic system of claim 1, further comprising a sensor to generate a signal indicative of a manual demonstration of a desired range of motion of the remotely controllable arm, wherein the processor is configured to operate the positioning indicator to direct the manual repositioning of the base relative to the floor surface by:

directing the manual repositioning of the base based on the signal indicative of the manual demonstration.

14. The robotic system of claim 1, wherein the processor is configured to operate the positioning indicator to direct the manual repositioning of the base relative to the floor surface by:

directing the manual repositioning of the base based on a location of an obstacle on the floor surface relative to the base; or directing the manual repositioning of the base based on a location of an end of a rail relative to the base, wherein the base is movable along the rail.

15. The robotic system of claim 1, further comprising a second remotely controllable arm communicatively coupled to the processor, the second remotely controllable arm configured to support and position a second tool, the second remotely controllable arm having a second powered joint operable to move the second tool, wherein the processor is further configured to:

operate the second powered joint to maintain a position of a distal portion of the second remotely controllable arm during the manual repositioning.

16. The robotic system of claim 1, wherein the processor is configured to operate the positioning indicator to direct the manual repositioning of the base relative to the floor surface by:

directing the manual repositioning of the base based on a pose of the remotely controllable arm relative to a pose of a second remotely controllable arm.

17. The robotic system of claim 1, wherein the processor is configured to operate the positioning indicator to direct the manual repositioning of the base relative to the floor surface by:

directing a first manual repositioning of the base before the tool is inserted into an access port of a patient; and directing a second manual repositioning of the base after the tool is inserted into the access port.

18. The robotic system of claim 1, wherein the processor is configured to operate the powered joint to maintain the position of the distal portion of the remotely controllable arm during the manual repositioning by:

operating the powered joint to maintain the position of the distal portion relative to a first reference point before the tool is inserted into an access port; and operating the powered joint to maintain the position of the distal portion relative to a second reference point after the tool is inserted into the access port, the second reference point corresponding to a position of the access port.

19. The robotic system of claim 1, further comprising a movable table configured to support a patient above the floor surface, wherein the processor is further configured to:

operate the positioning indicator to direct a manual repositioning of the movable table; and operate the powered joint to maintain the position of the distal portion of the remotely controllable arm during the manual repositioning of the movable table.

20. The robotic system of claim 1, wherein the processor is further configured to operate the positioning indicator to indicate an estimated distance between an optimal location of the base and a current location of the base.

21. A method of operating a robotic system comprising a robotic arm extending from a base, the method comprising:

determining, by a processor, a target base pose of the base;

operating, by the processor, a positioning indicator to direct a manual repositioning of the base relative to a floor surface; and operating, by the processor, the robotic arm to maintain a position of a distal portion of the robotic arm during the manual repositioning of the base.

22. The method of claim 21, further comprising:

operating, by the processor, the robotic arm to maintain an orientation of the distal portion of the robotic arm during the manual repositioning of the base.

23. The method of claim 21, wherein operating the robotic arm to maintain the position of the distal portion of the robotic arm during the manual repositioning of the base comprises:

operating the robotic arm to maintain the position of the distal portion relative to a location of an access port; or operating the robotic arm to maintain a position of a cannula being held by the robotic arm; or operating the robotic arm to maintain a position of a tool being supported by the robotic arm.

24. The method of claim 21, further comprising:

operating, by the processor, a braking mechanism to inhibit movement of the base away from an optimal base location envelope.

25. The method of claim 21, wherein operating the robotic arm to maintain the position of the distal portion of the robotic arm during the manual repositioning of the base comprises:

concurrently operating, by the processor, a powered joint of the robotic arm and a release mechanism of a passive joint of the robotic arm.

26. The method of claim 21, wherein operating the positioning indicator to direct the manual repositioning of the base relative to the floor surface comprises:

operating, by the processor, an actuator or a brake to inhibit movement of the robotic arm and provide a tactile indication to direct the manual repositioning of the base.

27. The method of claim 21, wherein determining, by the processor, the target base pose of the base comprises:

determining the target base pose based on at least one of: a signal indicative of a manual demonstration of a desired range of motion of the robotic arm, a location of an obstacle and a pose of a second robotic arm, and a location of an end of a rail to which the base is movably mounted.

28. A non-transitory machine-readable medium comprising a plurality of machine-readable instructions which when executed by one or more processors associated with a robotic system comprising a robotic arm extending from a base, are adapted to cause the one or more processors to perform a method comprising:

determining a target base pose of the base;

operating a positioning indicator to direct a manual repositioning of the base relative to a floor surface; and operating the robotic arm to maintain a position of a distal portion of the robotic arm during the manual repositioning of the base.

29. The non-transitory machine-readable medium of claim 28, wherein the method further comprises:

operating the robotic arm to maintain an orientation of the distal portion of the robotic arm during the manual repositioning of the base.

30. The non-transitory machine-readable medium of claim 28, wherein operating the positioning indicator to direct the manual repositioning of the base relative to the floor surface comprises:

operating an actuator or a brake to inhibit movement of the robotic arm and provide a tactile indication to direct the manual repositioning of the base.

* * * * *